United States Patent
Branch et al.

(10) Patent No.: US 9,096,823 B1
(45) Date of Patent: Aug. 4, 2015

(54) MICROFLUIDIC DEVICE FOR ACOUSTIC CELL LYSIS

(75) Inventors: Darren W. Branch, Albuquerque, NM (US); Erika Jane Cooley, Albuquerque, NM (US); Gennifer Tanabe Smith, Albuquerque, NM (US); Conrad D. James, Albuquerque, NM (US); Jaime L. McClain, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 974 days.

(21) Appl. No.: 12/872,919

(22) Filed: Aug. 31, 2010

(51) Int. Cl.
| | |
|---|---|
| C12M 1/42 | (2006.01) |
| C12M 1/00 | (2006.01) |
| C12N 1/06 | (2006.01) |
| B01F 13/00 | (2006.01) |
| B01F 11/02 | (2006.01) |
| B01J 19/10 | (2006.01) |
| G01N 35/00 | (2006.01) |
| C12M 3/06 | (2006.01) |

(52) U.S. Cl.
CPC .............. *C12M 47/06* (2013.01); *C12N 1/066* (2013.01); *B01F 11/0241* (2013.01); *B01F 13/0059* (2013.01); *B01J 19/10* (2013.01); *B01L 2400/0439* (2013.01); *C12M 23/16* (2013.01); *G01N 2035/00554* (2013.01)

(58) Field of Classification Search
CPC ...... C12M 23/16; C12M 45/02; C12M 35/04; C12M 47/06; C12M 27/16; C12M 33/08; B01L 2400/0439; G01N 2035/00554; B01F 11/0241; B01F 13/0059; B01F 13/0074; B01J 19/0093; B01J 19/10; C12N 1/066; C12N 15/1017

USPC .................. 435/287.2, 288.5, 306.1
See application file for complete search history.

(56) References Cited

U.S. PATENT DOCUMENTS

| | | | |
|---|---|---|---|
| 6,168,948 B1* | 1/2001 | Anderson et al. .......... 435/287.2 |
| 6,789,426 B2* | 9/2004 | Yaralioglu et al. .............. 73/597 |
| 7,731,412 B2* | 6/2010 | Sparey-Taylor et al. ...... 366/127 |
| 7,785,868 B2* | 8/2010 | Yuan et al. ................. 435/306.1 |
| 2011/0166551 A1* | 7/2011 | Schafer ........................ 604/522 |

FOREIGN PATENT DOCUMENTS

WO WO 2007041671 A2 * 4/2007

OTHER PUBLICATIONS

Marentis et al. "Microfluidic Sonicator for Real-Time Disruption of Eukaryotic Cells and Bacterial Spores for DNA Analysis." Ultrasound in Med. and Biol., vol. 31, No. 9 (2005), pp. 1265-1277.*

(Continued)

*Primary Examiner* — William H Beisner
(74) *Attorney, Agent, or Firm* — Kevin W. Bieg

(57) ABSTRACT

A microfluidic acoustic-based cell lysing device that can be integrated with on-chip nucleic acid extraction. Using a bulk acoustic wave (BAW) transducer array, acoustic waves can be coupled into microfluidic cartridges resulting in the lysis of cells contained therein by localized acoustic pressure. Cellular materials can then be extracted from the lysed cells. For example, nucleic acids can be extracted from the lysate using silica-based sol-gel filled microchannels, nucleic acid binding magnetic beads, or Nafion-coated electrodes. Integration of cell lysis and nucleic acid extraction on-chip enables a small, portable system that allows for rapid analysis in the field.

19 Claims, 19 Drawing Sheets

(56) References Cited

OTHER PUBLICATIONS

Norris et al., "Acoustic Differential Extraction for Forensic Analysis of Sexual Assault Evidence." Anal. Chem., vol. 81 (2009), pp. 6089-6095.*

P. Belgrader, "A Minisonicator to Rapidly Disrupt Bacterial Spores for DNA Analysis," Anal. Chem. 1999, 71, 4232-4236.

R. Boom, "Rapid and Simple Method for Purification of Nucleic Acids," J. of Clinical Microbiology, Mar. 1990, vol. 28, No. 3, 495-503.

N. C. Cady, "Nucleic acid purification using microfabricated silicon structures," Biosensors and Bioelectronics 19 (2003) 59-66.

D. P. Chandler, "Continuous Spore Disruption Using Radially Focused, High-Frequency Ultrasound," Anal. Chem. 2001, 73, 3784-3789.

H. Jagannathan, "Micro-Fluidic channels with Integrated Ultrasonic Transducers," 2001 IEEE Ultrasonics Symposium, 859-862.

M. Lee, "Reversible capture of genomic DNA by a Nafion-coated electrode," Analytical Biochemistry 380 (2008) 335-337.

M. More, "Quantitative Cell Lysis of Indigenous Microorganisms and Rapid Extraction of Microbial DNA from Sediment," Applied and Environmental Microbiology, May 1994 1572-1580.

D.W. Branch, "Intelligent Front-end Sample Preparation Tool Using Acoustic Streaming," Sandia Nat'l. Labs Report SAND2009-6193, Sep. 2009.

K. A. Wolfe, "Toward a microchip-based solid-phase extraction method for isolation of nucleic acids," Electrophoresis 2002, 23, 727-733.

G. Zhang, "Liquid Streaming by High-Frequency Ultrasonic Waves," Jpn. J. Appl. Phys. vol. 35 (1996) 3248-3250.

\* cited by examiner

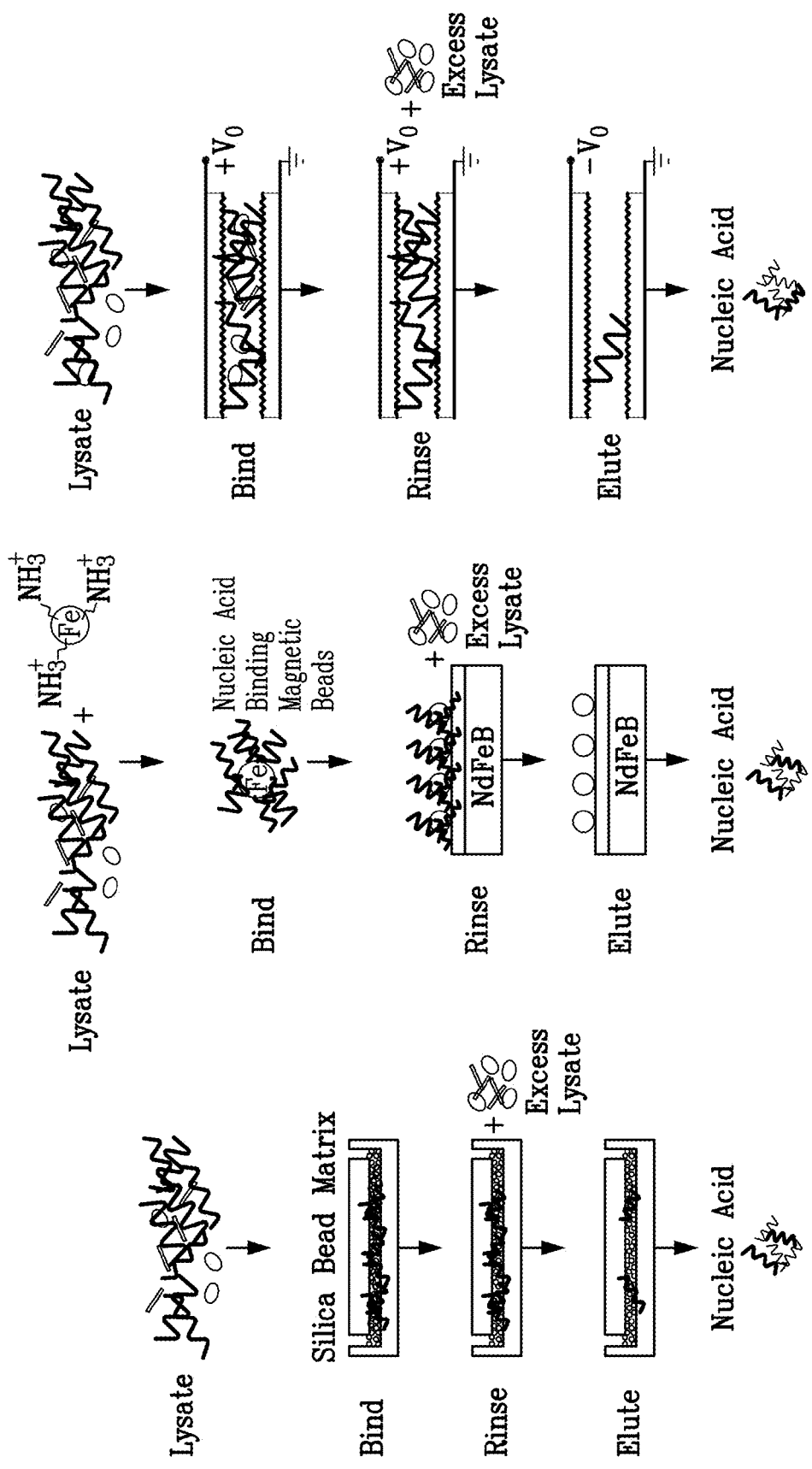

MICROFLUIDIC DEVICE FOR ACOUSTIC CELL LYSIS

STATEMENT OF GOVERNMENT INTEREST

This invention was made with Government support under contract no. DE-AC04-94AL85000 awarded by the U. S. Department of Energy to Sandia Corporation. The Government has certain rights in the invention.

FIELD OF THE INVENTION

The present invention relates to the lysis of biological cells and, in particular, to a microfluidic device and method for cell lysis by localized acoustic pressure.

BACKGROUND OF THE INVENTION

The need to rapidly extract and process genomic material for identification of biological agents and disease is an ever increasing requirement. Methods that allow the complete unbiased isolation of nucleic acids from microorganisms and cellular samples are necessary to aid in molecular analysis methods and detection schemes. The biases implicit in samples makes it essential to develop preparation methods that directly access the nucleic acid content for field portable systems. This requires overcoming a variety of interferences that diminish quality, yield, and diversity of extracted nucleic acids. Routine laboratory methods for cell lysis include freeze/thaw, proteinase K, lysozyme, and guanidium salt treatments followed by ethanol or 2-propanol precipitation of liberated DNA; ballistic disintegration; and sonication at low frequencies (e.g., kilohertz) after pretreatment with other chemicals. See D. P. Chandler et al., *Anal. Chem.* 73, 3784 (2001).

For field portable systems, the tendency has been to simply downscale laboratory-scale equipment in genetic engineering to microscale on-chip processing. Therefore, a key aspect is that the extraction format must be highly scalable to benefit from many types of biodetection systems that are already in place. Many of the current nucleic acid extraction techniques, however, require significant manual intervention and consumables leading to limitations that are especially relevant for the unattended, timely detection of biological warfare agents or other microorganisms in a complex milieu. The continued reliance on large laboratory equipment (e.g., centrifuges, gel electrophoresis units, ultracentrifuges), requirements for chemical or enzymes that are labile or need special handling, and storage and disposal, further impede progress toward miniaturized autonomous detection.

Microsystems have been developed that use mechanical, chemical, thermal, and chemical methods for cell lysis. Ultrasonic waves are known to induce significant pressure variation and induce cavitation within fluids. See G. Zhang et al., *Jpn. J. Appl. Phys.* 35, 3248 (1996). Thus, acoustic waves can provide a non-invasive lysing mechanism which is compatible with sealed microsystems. Acoustic methods avoid the use of harsh chemicals which often interfere with subsequent detection methods (e.g., PCR). Often the altered pH and chemical background adds additional steps that can otherwise be avoided. Recently, large-scale acoustic transducers have proven powerful for disrupting cell membranes and spores and releasing the contents of the cytoplasm for subsequent DNA analysis. See D. P. Chandler et al.; and P. Belgrader et al., *Anal. Chem.* 71, 4232 (1999). Thin-film based ultrasonic actuators have also been used to lyse cellular samples and have proven effective for microsystem applications. See T. C. Marentis et al., *Ultrasound in Med. & Biol.* 31, 1265 (2005); and H. Jagannathan et al., *IEEE Ultrason. Symp.,* 859 (2001). However, small-scale actuators suffer from limitations in attainable film thickness and meeting the thermal requirements for long-term use. The deposition thicknesses that can be reasonably attained are between 1 to 10 which translates to range of 316 MHz to 3.165 GHz for ZnO. However, a frequency of less than 300 MHz is far more optimal for coupling into the fluid. Moreover, these devices must be strictly operated in a pulsed mode to prevent device damage.

A second major problem is that nearly all microsonicator approaches lack on-chip nucleic acid extraction processing capability. Thus, the lysate must be processed and purified off-chip, reducing the effectiveness of a microsystem solution. Nucleic acid purification methods that are suitable for on-chip applications require the use of silicon based microstructures, commercial nucleic acid binding media, silica beads in the presence of chaotropic salts, and silica matrices. See N. C. Cady et al., *Biosens. Bioelectr.* 19, 59 (2003); M. Moré et al., *Appl. Environ. Microbiol.* 60, 1572 (1994); R. Boom et al., *J. Clin. Microbiol.* 28, 495 (1990); and K. Wolfe et al., *Electrophoresis* 23, 727 (2002). Though packed silica beads bind and elute nucleic acids, their inherent instability due to compression causes widely varying results. This limitation has been overcome by using a gelled sol-gel solution of silica beads to stabilize the matrix, improving reproducibility. Recently another powerful nucleic acid extraction method has been demonstrated which uses NAFION coated gold films to reversibly capture nucleic acids. See M. Lee et al., *Anal. Biochem.* 380, 335 (2008). This method is particularly easy to implement in microfluidic format and only needs low DC voltages for operation.

Therefore, a need remains for an acoustic-based microfluidic lysing device that can be integrated with an on-chip nucleic acid extraction processing capability and can be used in a field portable system.

SUMMARY OF THE INVENTION

The present invention is directed to an acoustic-based microfluidic device for cell lysis comprising a channel formed in a microfluidic substrate, adapted to flow a fluid comprising biological cells therein; and at least one acoustic transducer disposed on a lysis portion of the channel, adapted to generate localized acoustic pressure in the lysis portion and thereby lyse the biological cells in the fluid by acoustic pressure. The transducer array can use 36° Y cut lithium niobate, which efficiently couples bulk acoustic waves (BAW) into the channels. The height of the channel can be than ten acoustic wavelengths and preferably less than 100 microns. The operating frequency of the acoustic transducers can be less than 100 MHz. A heat sink can be provided for removal of heat generated by the acoustic transducers from the device to avoid thermal lysis or protein denaturization. The microfluidic substrate preferably comprises a rigid material, such as plastic, glass, ceramic, or a silicon-based material. The channel can be a straight channel or can be a circuitous or serpentine channel to increase the exposure time to the acoustic pressure field. Preferably, the acoustic transducer array is disposed on a separate array substrate that is reversibly coupled to a microfluidic cartridge comprising the channel formed in the microfluidic substrate to enable reuse of the transducer assembly while permitting disposal of the contaminated fluidic cartridges. The acoustic transducer array can efficiently and rapidly lyse samples for either subsequent use or further processing on the cartridge.

The device can further comprise a nucleic acid extraction portion formed in the microfluidic substrate downstream from the lysis portion, adapted to extract nucleic acid from the lysate. The nucleic acid extraction portion can comprise means for extracting the nucleic acid from the lysate using a sol-gel/silica bead matrix, nucleic acid binding magnetic beads, or electric field extraction with NAFION-coated electrodes. Successful lysing and DNA extraction from *E. coli* samples in plastic and glass based microfluidic cartridges has been demonstrated at levels sufficient for molecular beacon and PCR detection applications.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 4 shows cross-section illustrations of a BAW transducer and composite structure.

FIG. 15 shows nucleic acid extraction methods. FIG. 15a is a schematic illustration of a sol-gel silica bead matrix based extraction method. FIG. 15b is a schematic illustration of a magnetic bead based nucleic acid extraction method. FIG. 15c is a schematic illustration of a NAFION-coated electrode based extraction method.

DETAILED DESCRIPTION OF THE INVENTION

The present invention is directed to a microfluidic acoustic-based cell lysing device that can be integrated with on-chip nucleic acid extraction. Using a bulk acoustic wave (BAW) transducer array, acoustic waves can be coupled into microfluidic cartridges resulting in the lysis of cells contained therein by acoustic pressure. Cellular materials can then be extracted from the lysed cells. For example, nucleic acids can be extracted from the lysate using silica-based sol-gel filled microchannels, nucleic acid binding magnetic beads, or NAFION-coated electrodes. Integration of cell lysis and nucleic acid extraction on-chip enables a small, portable system that allows for rapid analysis in the field.

Figure 1:
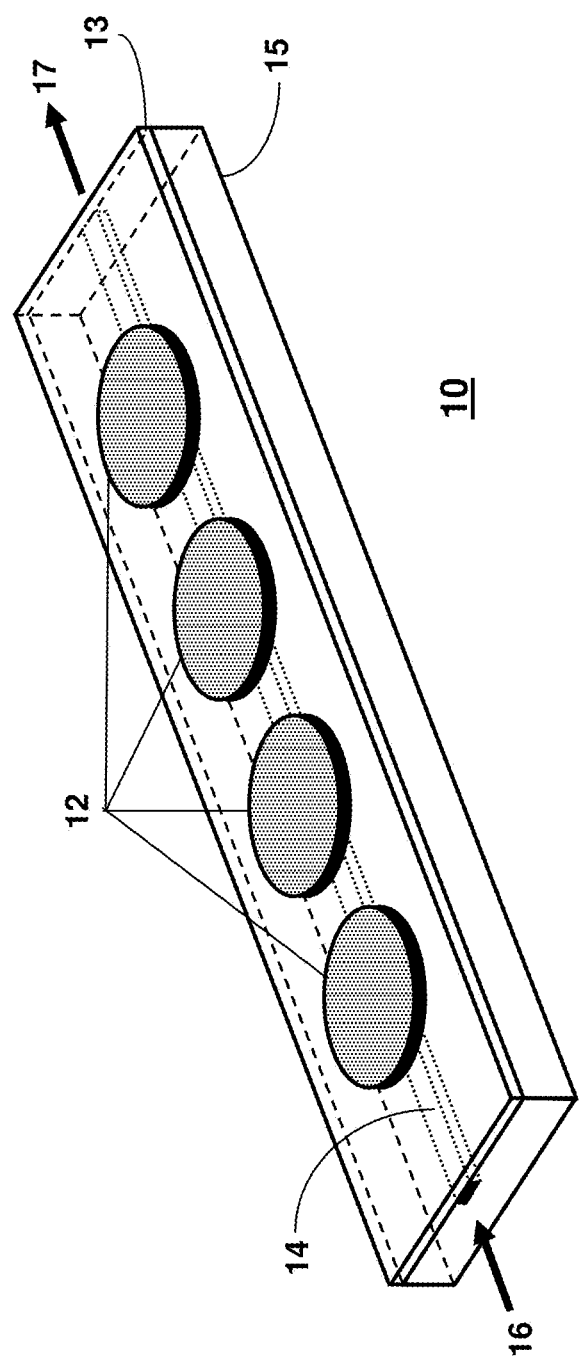
FIG. 1 is a perspective top-view schematic illustration of a microfluidic acoustic lysing device.

FIG. 1 shows a perspective top-view schematic illustration of a device 10 that can be used for cell lysis by localized acoustic pressure. The acoustic-based microfluidic lysing device 10 comprises at least one acoustic transducer 12 disposed on a top lid 13 of a channel 14 that is formed in a microfluidic substrate 15. Whole cells can enter the channel 14 through an inlet 16 and are lysed by acoustic pressure in the channel generated by the array of acoustic transducers 12. The BAW transducer array can be monolithically integrated with the microfluidic channel on the same substrate. Alternatively, a modular device can comprise the BAW transducer array fabricated on a substrate that can be reversibly coupled to a separate cartridge comprising the microfluidic channel. Reversible coupling of a microfluidic cartridge to the BAW transducer array enables reuse of the transducer assembly while permitting disposal of the contaminated microfluidic cartridge. The microfluidic cartridge can further provide the necessary fluidics to mix the lysate with a nucleic acid extraction portion downstream from the acoustic lysing portion. Lysate containing the acoustically lysed cells can exit the channel 14 through an outlet 17. A heat sink (not shown) can be disposed on top of the acoustic transducers and microchannel for removal of heat from the device to inhibit thermal lysis of the cells flowing in the microfluidic channel.

The substrate 15 can comprise a microfluidic material that is preferably rigid to minimize acoustic loss. For example, the substrate 15 can comprise plastic, glass, ceramic, or a silicon-based material. The channel 14 can be a straight channel, or can have a circuitous pattern (e.g., serpentine) to increase the exposure time to the acoustic pressure field. The channel 14 can be formed in the substrate by microfabrication methods that are known in the art. For example, a channel can be formed in polydimethylsiloxane (PDMS) by a standard molding process. Alternatively, a channel 14 can be formed in a glass, ceramic, or silicon-based substrate by bulk or surface micromachining. Preferably, the acoustic wavelength in the fluid is comparable to comparable to the size of the cells to be lysed. The height of the channel is preferably comparable to the acoustic attenuation length in the fluid and depends on the excited wavelength for optimal propagation distance. For example, the height can preferably be less than ten acoustic wavelengths in the fluid and, more preferably a few acoustic wavelengths. The width of the channel is preferably smaller than the acoustic transducer to maintain lysing uniformity.

Figure 2:
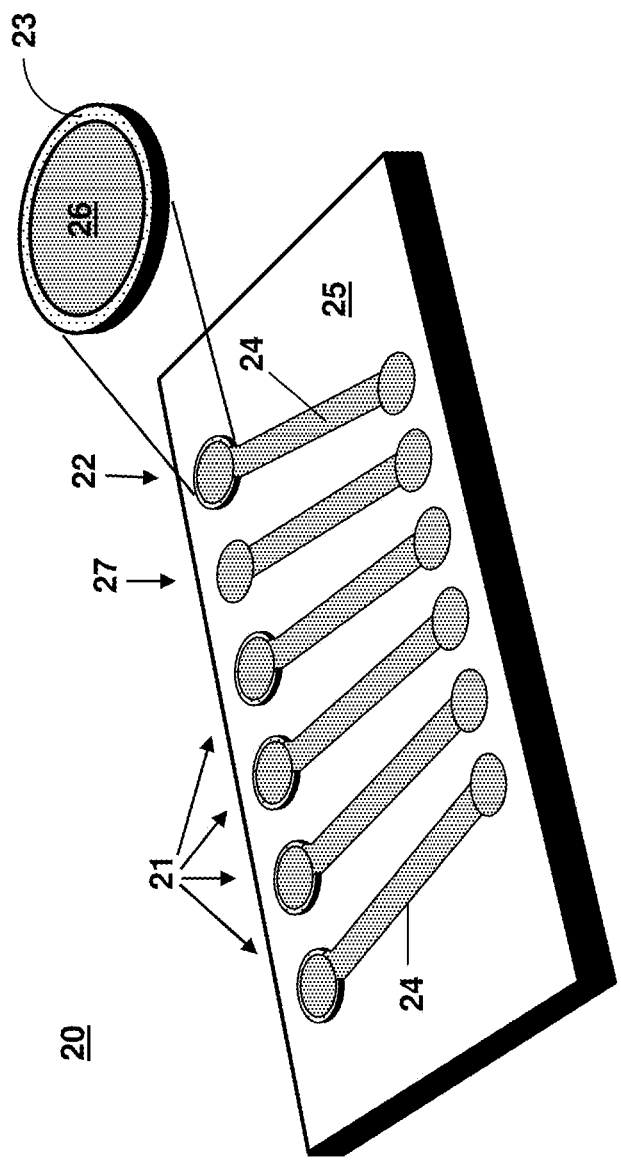
FIG. 2 is a perspective top-view schematic illustration of a bulk acoustic wave (BAW) transducer array.

FIG. 2 shows a schematic illustration of an exemplary BAW transducer array 20 that can be reversibly coupled to a microfluidic cartridge. In this example, four acoustic transducers 21 can be used for cell lysis and a final transducer 22 can be used for mixing solutions in a chamber downstream from the lysing portion of the channel. Each transducer 21 or 22 comprises a piezoelectric substrate 23 sandwiched between two electrodes. Electrical connections to the piezoelectric substrates can be made by depositing electrodes and contact pads onto an array substrate 25. A bottom electrode and contact pad 24 for each transducer 21 or 22 can be patterned on the substrate 25 by a shadow mask process. A ground electrode and contact pad 27 can also be patterned on the substrate 25. Each piezoelectric transducer can also comprise a top electrode 26 on the top surface of each piezoelectric substrate 23. The transducers 21 and 22 couple energy to the channel 14 through the substrate boundary with the microfluidic cartridge, whereby remote actuation of the fluid in the channel is accomplished by the propagation of acoustic waves therein.

Figure 3:
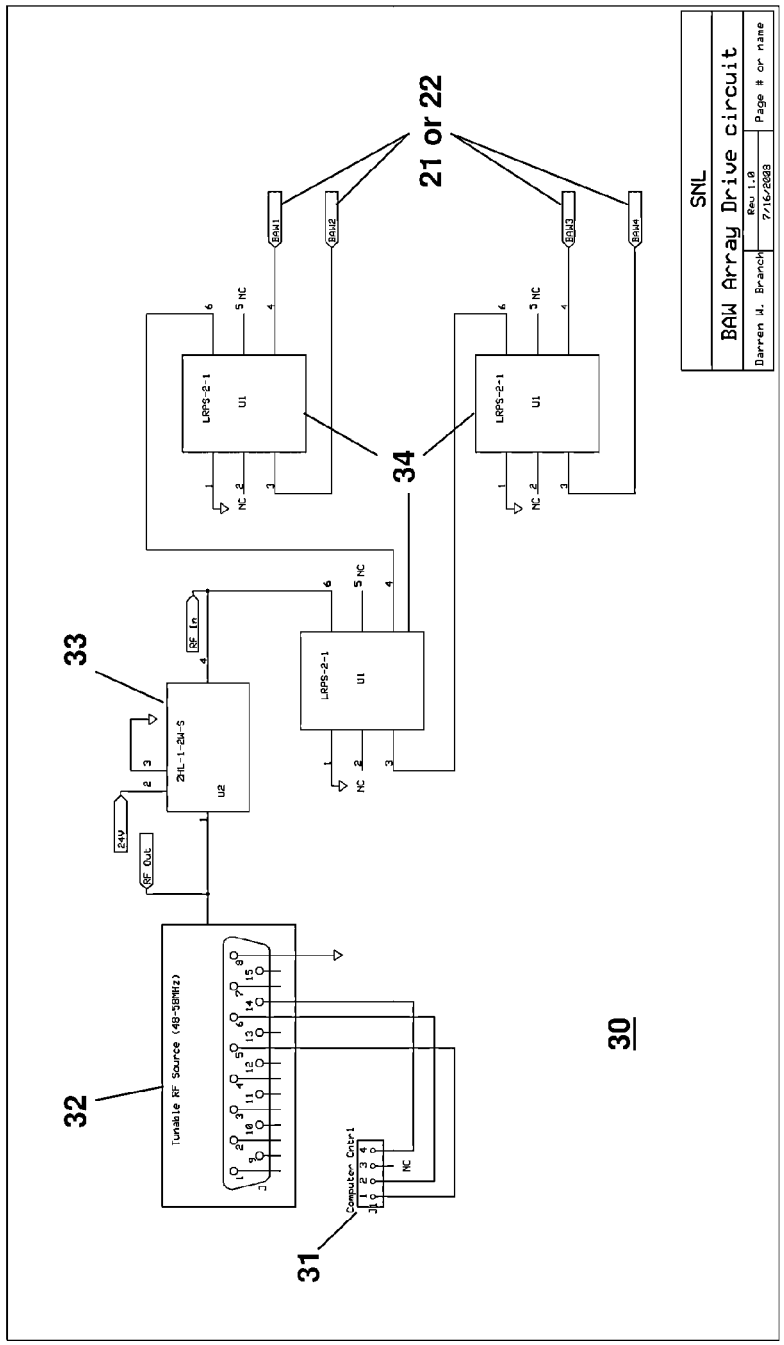
FIG. 3 is a schematic of a radio frequency (RF) drive circuit for a microfluidic lysing device.

FIG. 3 shows a schematic illustration of an RF circuit 30 that can be used to drive the BAW transducers 21. Computer control 31 can be used to tune the frequency of an RF source 32. Frequency tuning can be desirable to account for changes in the fabrication process due to variations in transducer mass loading and bonding. In this example, the RF drive circuit 30 comprises an RF source 32 that can be tuned from 48 to 58 MHz. The RF source 32 is connected to an RF power amplifier 33 (e.g., 2 W). The amplifier output can be split by power dividers 34 to drive each of the BAW transducers 21 (e.g., four in this array). The power input can thereby be configured at deliver a maximum power (e.g., 200 mW) to each transducer.

A scattering parameter S11 can be used to characterize the electrical performance of the BAW transducer array prior to assembly with the microfluidic cartridge. S11 is a complex-valued quantity that is equivalent to the measured reflection coefficient, and from which the power delivered to the device can be calculated. For example, S11 can be recorded across a 10 MHz-100 MHz band using a network analyzer. The power delivered to the device can be chosen to maximize lysing efficiency without causing cavitation or excessive heating of the transducer and heat sink. Thermal effects can dramatically limit the success of any acoustic-based lysing system, specifically where the protein content may be of interest.

Modeling of the Microfluidic Lysing Device

A 1D transmission line model and a finite element method (FEM) can be used to calculate the acoustic pressure and velocity fields in the fluid-filled channel. Using these computed fields, the kinetic and potential energies can be calculated. This enables determination of the force profile within the channel. The acoustic transducers can be designed to create large pressure fields (~10 MPa) in a microfluidic channel to achieve efficient lysing. It is preferable that the lysing mechanism occur due to the acoustic pressure field alone, rather than from localized heating during acoustic excitation. Therefore, additional layers and thermal management can be used for impedance matching while mitigating any heat generated by the acoustic transducers.

Figure 4A:
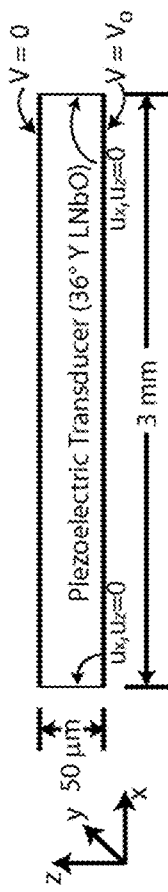
FIG. 4a is a cross-sectional end view illustration of an unloaded transducer.
Figure 4B:
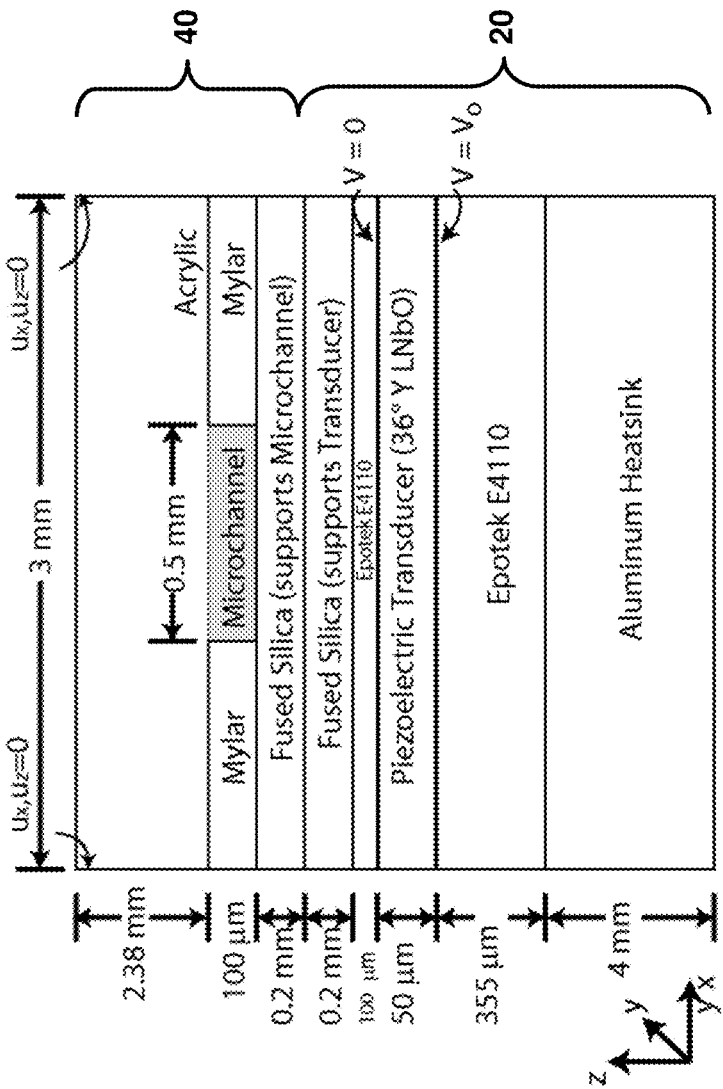
FIG. 4b is a cross-sectional end view illustration a composite structure comprising layers that permit removal of a microfluidic cartridge from a BAW transducer array.

FIG. 4 shows cross-sectional end-view illustrations of a BAW transducer and composite structure that were modeled using the 1D transmission line model and FEM. FIG. 4a shows a cross-section end view illustration of an unloaded BAW transducer. FIG. 4b shows a cross-section end view illustration of a composite structure that enables removal of a microfluidic cartridge 40 from a BAW transducer array 20. In this example, the piezoelectric transducer comprises a 36° Y LNBO substrate that is approximately 50 μm thick and 3 mm in diameter. A bottom electrode can be made by patterning a 2000 Å thick Au/Cr electrode (not shown) on a 0.2 mm thick fused silica substrate using a shadow mask deposition process. The piezoelectric substrate can be bonded to the gold bottom electrode using a conductive epoxy. In this example, the LNBO substrate can be bonded to the gold electrode (not shown) using a 100 μm thick layer of Epotek E4110 conductive epoxy. The piezoelectric substrate and bottom gold electrode and contact pad can then be encapsulated, leaving an opening on the backside of the piezoelectric substrate for a top electrode. The exposed open region can be filled with conductive epoxy (e.g., 355 μm thick coating of Epotek 4110) to provide a top electrode. A voltage $V_o$ can be applied between the top and bottom electrodes. A heat sink (e.g., 4 mm thick aluminum) can be bonded above the transducer using a thermally conductive epoxy. This heat sink can remove heat from the lysing region and the acoustic transducers. In this example, the microfluidic cartridge comprises a 0.5 mm wide×100 μm high channel formed in a 100 μm thick Mylar film sandwiched between a 0.2 mm thick fused silica substrate and a 2.38 mm thick acrylic layer.

Piezoelectric Field Equations

Acoustic waves must satisfy both Newton's and Maxwell's equations. In the absence of external forces, the equations are expressed as $$\rho \frac{\partial^2 u_i}{\partial t^2} = \nabla \cdot T \tag{1}$$

$$S = \nabla_s u \tag{2}$$

$$\nabla \cdot D = \rho_f \tag{3}$$

where ρ is the mass density, u is the particle displacement, and T and S are the surface stress and strain components, respectively. D and $\rho_f$ are the electric displacement and free charge density, respectively. The free charge density $\rho_f$ is zero everywhere except at the surface of the piezoelectric substrate.

In a piezoelectric substrate, the coupled constitutive equations for piezoelectric media are given by $$T_{ij} = c_{ijkl}^E S_{kl} - e_{kij}^t E_k \tag{4}$$

$$D_i = e_{ikl} S_{kl} + \epsilon_{ik}^S E_k \tag{5}$$

where e and $c^E$ are the piezoelectric stress constants and stiffness constants. Since the coupling between the electric and elastic fields is weak, the magnetic fields can be neglected and the electric fields can be derived from the scalar potential. This is known as the static field approximation in which the particle displacements $u_i$ are along the coordinate axis $x_i$. Eqs. (4) and (5) recognize Hooke's law, and D=∈E, where E=−∇φ and φ is the electrical potential on the surface. Substituting Eqs. (4) and (5) into Eqs. (1) and (2) yields $$\rho \frac{\partial^2 u}{\partial t^2} = \nabla \cdot c^E : \nabla_s u - \nabla \cdot (e \cdot E) \tag{6}$$

$$\nabla \cdot (e : \nabla_s u) - \nabla \cdot (\varepsilon^s \cdot \nabla \phi) = 0 \tag{7}$$

Finite Element Method

In the FEM formalism for piezoelectricity, the partial differential equations that relate the stresses to the particle displacement and the electric displacement to the free volume charge density are replaced with finite number of unknowns and used to solve Eqs. (4) and (5). See H. Allik and T. J. R.

Hughes, *Int. J. Numer. Methods Eng.* 2, 15 (1970). The piezoelectric transducer was analyzed using a multiphysics FEM tool. A triangular mesh was used for the entire structure.

In the fluid region the acoustic waves are governed by the frequency-domain Helmholtz equation for determining the acoustic pressure $$\nabla \cdot \left(-\frac{1}{\rho_f}(\nabla p - q)\right) - \left(\frac{\omega^2}{\rho_f c_f^2}\right) p = Q \tag{8}$$

where p is the acoustic pressure (Pa), $\rho_f$ is the fluid density (kg/m$^3$), $c_f$ is the complex acoustic velocity (m/s) in the medium, $\omega$ is the angular frequency (rad/s), q is a dipole source term (N/m$^3$), and Q is the monopole source term (1/s$^2$). The inclusion of acoustic loss in the fluid region is introduced by allowing the fluid density ($\rho_f$) and acoustic speed ($c_f$) to be complex quantities $$\rho_f = \frac{Z_f k_f}{\omega} \quad c_f = \frac{\omega}{k_f} \quad k_f = \frac{\omega}{c_s} - i\alpha \quad Z_f = \rho_o c_s \tag{9}$$

where $Z_f$ is the complex acoustic impedance (Pa·s/m$^2$) and $\alpha$ is the attenuation coefficient (1/m). In the absence of damping (i.e., $\alpha$=0), $\rho_f = \rho_o$ and $c_f = c_s$.

In the model shown in FIG. 4, the piezoelectric transducer was excited by application of $V_o$=1 V to the top edge while the bottom surface had V=0, and the electrodes were modeled as infinitely thin. The edges of the transducer were fixed with the electrode surfaces allowed to move freely to approximate a real transducer. This boundary required that the displacements $u_x$ and $u_y$=0. The top and bottom surface of the transducer were free to move. Continuity of stresses and displacements were imposed on the internal boundaries of the aluminum heat sink, acrylic, piezoelectric transducer, and fused silica. The motion of the solid regions produces normal acceleration (a) at the interfaces between the fluid and acrylic layer given as $$a_x \cdot n_x + a_y \cdot n_y = n \cdot \left(\frac{1}{\rho_c}(\nabla p)\right) \tag{10}$$

This equation couples the motion of the transducer, aluminum, and fused silica layers into acceleration of the fluid. In turn, the fluid pressure produces a load on the acrylic and fused silica regions. This load was included since the fluid pressure is not negligible as in the case of an air domain in contact with the silicon. Fluid loads the acrylic and fused silica layers as $$F_x = -p \cdot n_x, F_y = -p \cdot n_y \tag{11}$$

where p is the pressure in the fluid (Na), and $n_x$ and $n_y$ are the normal components at the fluid-structure interfaces.

FEM Extraction of Electrical Impedance and Electromechanical Coupling

In the 2D FEM analysis, the impedance was computed using $$Z(\omega) = \frac{V}{\sum_i n \cdot J_i(\omega)} \tag{12}$$

where V was the amplitude of the driving voltage (V), and n·J is the current density outflow (A/m$^2$) at the nodes along the driven electrode boundary. The current density was computed on the driven electrode at each frequency. For comparison with measurement the impedance was converted to return loss (scattering parameter S11), $$S11(\omega) = \frac{Z(\omega) - Z_o}{Z(\omega) + Z_o} \tag{13}$$

where $Z_o$ is the load impedance (typically 50Ω). The piezoelectric coupling coefficient was calculated from the material parameters as $$K_{33} = \sqrt{\frac{e_{33}^2}{\varepsilon_0 \varepsilon_r^s c_{33}^E + e_{33}^2}} \tag{14}$$

where $e_{33}$ is the piezoelectric coefficient (C/m$^2$), $\epsilon_0$ is the permittivity of free space, $\epsilon_r^s$ is the relative permittivity at constant strain, and $c_{33}^E$ is the stiffness at constant electric field. (Note: this piezoelectric coupling coefficient differs from κ which is defined as $$K = \sqrt{e_{33}^2 | \epsilon^S C^E}$$

with $c^E = c^D - e^2 | \epsilon^S$).

From the FEM results the piezoelectric coupling was computed as $$K_{33(FEM)} = \sqrt{\frac{\pi}{2} \frac{f_r}{f_a} \tan\left[\left(\frac{f_r - f_a}{f_a}\right)\frac{\pi}{2}\right]} \tag{15}$$

where $f_r$ is the resonant frequency and $f_a$ is the anti-resonant frequency of the transducer.

The material constants for 36° Y-cut lithium niobate are shown in Table 1. For propagation along the z-axis, the longitudinal velocity was computed from the material constants in the Table as v=7340 m/s for the thickness extension mode. For fused silica, the material constants are E=70×10$^9$ N/m$^2$, Y=0.17, and ρ=2200 kg/m$^3$. The material constants for acrylic are E=9×10$^9$ N/m$^2$, Y=0.37, ρ=1190 kg/m$^3$, α=6.4 dB/cm @ 5 Mhz. For Mylar, the material constants are E=7.6×10$^9$ N/m$^2$, Y=0.37, and ρ=1190 kg/m$^3$. The water was modeled as an ideal fluid with $\rho_f$=1000 kg/m$^3$ and $c_f$=1500 m/s. The material constants for the *E. coli* were $\rho_p$=1050 kg/m$^3$, $c_p$=1700 m/s, and $r_p$=1 μm.

TABLE 1

Acoustic Properties of Transducer Materials

36° YX LNBO[1]

$c^E$
$$\begin{bmatrix} 16.54 & 1.048 & 1.081 & 0 & 0 & 0 \\ 1.048 & 16.54 & 1.081 & 0 & 0 & 0 \\ 1.081 & 1.081 & 15.31 & 0 & 0 & 0 \\ 0 & 0 & 0 & 2.500 & 0 & 0 \\ 0 & 0 & 0 & 0 & 2.500 & 0 \\ 0 & 0 & 0 & 0 & 0 & 3.030 \end{bmatrix} \times 10^{10} (N/m^2)$$

e
$$\begin{bmatrix} 0 & 0 & 0 & 0 & 12.00 & 0 \\ 0 & 0 & 0 & 12.00 & 0 & 0 \\ -1.351 & -1.351 & 18.92 & 0 & 0 & 0 \end{bmatrix} (C/m^2)$$

TABLE 1-continued

Acoustic Properties of Transducer Materials

| | |
|---|---|
| $\epsilon^S/\epsilon_o$ | $\begin{bmatrix} 799.2 & 0 & 0 \\ 0 & 799.2 & 0 \\ 0 & 0 & 670.5 \end{bmatrix}$ |
| $\rho$ | 7500 (kg/m$^3$) |
| Q | 250 |
| tan ($\delta$) | 0.4 (%) |
| Epotek 301[2] | |
| $V_b$ | 2650 (m/s) |
| $V_s$ | 1230 (m/s) |
| $\alpha_b$ | 9.5 (dB/mm) |
| $\alpha_s$ | 36 (dB/mm) |
| $\rho$ | 1150 (kg/m$^3$) |
| E4110 Epoxy[3] | |
| $V_b$ | 4052 (m/s) |
| $\alpha_b$ | 56.4 (dB/cm) |
| $\rho$ | 2905 (kg/m$^3$) |
| Gold[3] | |
| $V_b$ | 3200 (m/s) |
| $\alpha_b$ | 1.9 (dB/cm) |
| $\rho$ | 21400 (kg/m$^3$) |
| Fused Silica[3] | |
| $V_b$ | 5640 (m/s) |
| $\alpha_b$ | 0.1 (dB/cm) |
| $\rho$ | 2240 (kg/m$^3$) |

[1]The elasticity matrix is given in IEEE format as [x, y, z, yz, xz, xy].
[2]Measured at 30 MHz
[3]Measured at 5 MHz Energy and Acoustic Radiation Force In the microchannel, the pressure field results from the superposition of standing waves in the z-direction and waves in the x-direction that are inherently weaker due to lateral coupling. The overall pressure field is calculated using the 2D FEM method for a non-viscous fluid. The time averaged energy density (J/m$^3$) in the fields is then split into the kinetic and potential which are given by $$\langle \overline{E}_k(x, y) \rangle = \frac{\rho_f}{2} \langle v^2(x, y) \rangle \qquad (16)$$

$$\langle \overline{E}_p(x, y) \rangle = \frac{1}{2\rho_f c_f^2} \langle |p(x, y)|^2 \rangle$$

Using these expressions, the force due to a local plane wave acting on a spherical particle in a fluid can be derived from the field potential U (J/m$^3$) in 2D, $$\langle U \rangle = 2\pi r^3 \rho_f \left( \frac{f_1}{3\rho_f c_f^2} \langle |p(x, y)|^2 \rangle - \frac{f_2}{2} \langle v(x, y) \rangle^2 \right) \qquad (17)$$

$$f_1 = 1 - \frac{\rho_f c_f^2}{\rho_s c_s^2} \quad f_2 = \frac{2(\rho_s - \rho_f)}{2\rho_s + \rho_f}$$

$$\langle F(x, y) \rangle = -\nabla \langle U(x, y) \rangle$$

where $\rho_s$ and $c_s$ are the particle density (kg/m$^3$) and acoustic speed (m/s) of the particle material. See L. P. Gor'kov, *Soviet Physics-Doklady* 6, 773 (1962). This expression is valid for all waves except progressive plane waves, giving the acoustic radiation force (N) acting on microparticles in the fluid. Other effects such as acoustic streaming, gravity, buoyancy, particle interactions, and particles near boundaries are ignored in the derivation of Eq. (17).

Thermal Analysis of Acoustic Transducer Array

To ensure cell lysis is dominated by an acoustic process, it is desirable to determine the thermal variation in the fluid and the associated heating of the composite structure. This was accomplished using a multiphysics model that coupled the Navier-Stokes incompressible flow to a convection and conduction model. The fluid flow in the microchannel was described by $$\rho(u \cdot \nabla)u + \nabla p - \nabla \cdot \eta(\nabla u + (\nabla u)^T) = 0 \qquad (18)$$

where u is the fluid velocity vector, $\eta$ is the viscosity, $\rho$ is the density, and p is the pressure. By accounting for energy transport through the entire structure, the heat carried by the fluid region, and the heat loss to the ambient media, the steady state thermal distribution can be computed.

The stationary thermal transport of convection and conduction was modeled using $$\nabla \cdot (-k\nabla T) = Q - \rho C_p u \cdot \nabla T \qquad (19)$$

where $C_p$ is the specific heat capacity, $\rho$ is the density, T is the temperature, and Q is a sink or source term. For the fully developed laminar flow condition, the following expression was used at the input port $$u = 16 \ u_{max} \frac{(z - z_o)(z_1 - z)(y - y_o)(y_1 - y)}{(z_1 - z_0)^2 (y_1 - y_o)^2} \qquad (20)$$

where y and z are the position within the channel, $y_o$ and $z_o$ define the beginning of the channel, and $y_1$ and $z_1$ defined the extent of the channel. At the outlet the heat is dominated by convection thus $$k\nabla T \cdot n = 0 \qquad (21)$$

With an inward heat flux boundary condition for the piezoelectric transducers, $$-n \cdot (q_1 - q_2) = q_o q_i = -k_i \nabla T_i \qquad (22)$$

the pressure condition was modeled as $$p_o = 0 \qquad (23)$$

and no slip at the microfluidic boundaries, $$u = 0 \qquad (24)$$

To couple the maximum velocity in the channel to the flow rate, the following expression was used $$f_{rate}[\mu l/min] = \text{fluid\_velocity}[cm/s] \cdot 6 \cdot 10^4 A_{cs}[cm] \qquad (25)$$

1D Transmission Line Model

Figure 5:
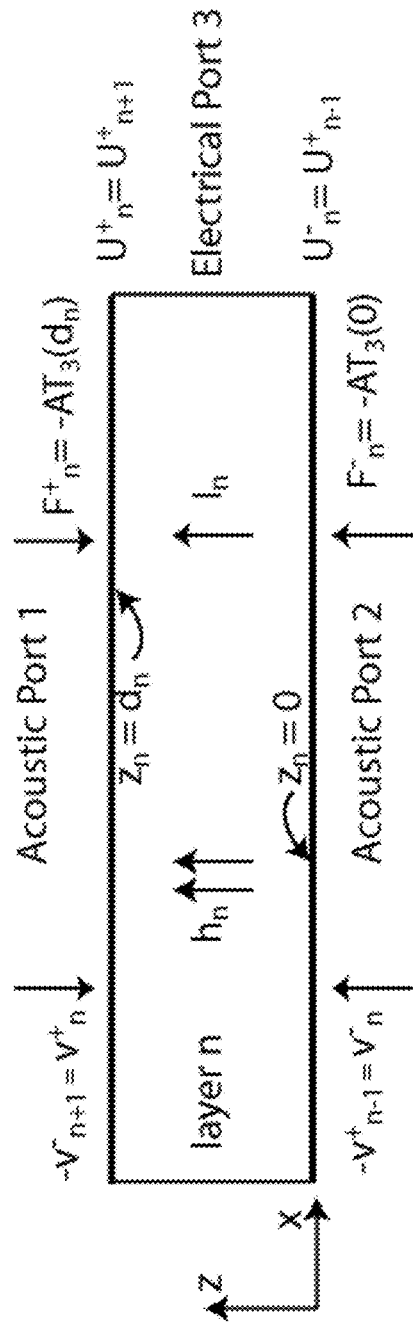
FIG. 5 shows the physical parameters of the $n^{th}$ piezoelectric layer of the transducer which is represented by a three port circuit in a 1D transmission line model.

For rapid modeling of piezoelectric and non-piezoelectric composites, a transmission line model offers significant advantages in computational speed. In FIG. 5, a single layer n is shown for a general acoustic transducer which may be piezoelectric or non-piezoelectric. The n$^{th}$ piezoelectric layer of the transducer is represented by a three port circuit. The 1D model assumes that the total thickness of the multilayer transducer is <10% of any lateral dimension. The velocity, force, potential, and current at the acoustic ports are $v_n$, $F_n$, $U_n$, and $I_n$. $h_n$ is the polarization of the material of layer n. In the 3×3 matrix formalism, forces and potential difference across the n$^{th}$ layer relates to the velocities and current at the n$^{th}$ layer. An electrical port defines a voltage across the thickness of a piezoelectric slab with two acoustic ports on each face of the piezoelectric plate. For a single piezoelectric layer, the forces at the interface can be expressed as $$F_1 = -AT(z_1) = ZA(ae^{-jkz_1} - be^{jkz_1}) - j\frac{h}{\omega}I \quad (26)$$

$$F_2 = -AT(z_2) = ZA(ae^{-jkz_2} - be^{jkz_2}) - j\frac{h}{\omega}I$$

The goal is to express the $F_1$ and $F_2$ in terms of the incoming velocities $v_1$ and $v_2$ at the faces of the layer, $$v_1 = v(z_1) = ae^{-jkz_1} + be^{jkz_1} \quad v_2 = v(z_2) = -ae^{-jkz_2} - bejkz2 \quad (27)$$

The voltage applied to the faces is determined by integrating the electric field E across the thickness of the transducer, $$U = \int_{z_1}^{z_2} E\,dz = -\int_{z_1}^{z_2} h\frac{\partial u}{\partial z} - \frac{D}{\varepsilon^S}\,dz = \frac{h}{j\omega}(v_1 + v_2) + \frac{I}{j\omega C_o} \quad (28)$$

$$C_o = \frac{\varepsilon^S A}{d}$$

By casting in matrix form the expressions (26), (27), and (28) were combined to give $$\begin{bmatrix} F_1 \\ F_2 \\ U \end{bmatrix} = \begin{bmatrix} -\frac{Z_o}{\tanh(\gamma d)} & \frac{Z_o}{\sinh(\gamma d)} & -\frac{h}{j\omega A} \\ -\frac{Z_o}{\sinh(\gamma d)} & \frac{Z_o}{\tanh(\gamma d)} & -\frac{h}{j\omega A} \\ \frac{h}{j\omega} & \frac{h}{j\omega} & \frac{1}{j\omega C_o} \end{bmatrix} \begin{bmatrix} v_1 \\ v_2 \\ I \end{bmatrix} \quad (29)$$

From this key result the electric impedance was derived for a layered system containing a single piezoelectric element by solving for U as a function of I, $$Z_e = \frac{1}{j\omega C_o} + \frac{h^2}{\omega^2 A}\left[\frac{2[\cosh(\gamma d)-1]Z_t + (Z_L + Z_R)\sinh(\gamma d)}{(Z_L Z_R + Z_t^2)\sinh(\gamma d) + Z_t(Z_L + Z_R)\cosh(\gamma d)}\right] \quad (30)$$

where $\gamma$ is the propagation constant, $Z_L$ is the total impedance loading on the left, $Z_R$ is the total impedance loading on the right, A is the cross sectional area, h is the stress piezoelectric constant (i.e., $e_{33}/\varepsilon_{33}$), and 4 is the acoustic impedance of the transducer. See J.-L. Dion et al., *IEEE Trans. Ultrason. Ferroelect. Freq. Contr.* 44, 1120 (1997); and P. E. Bloomfield et al., *IEEE Trans. Ultrason. Ferroelect. Freq. Contr.* 47, 1397 (2000). The acoustic attenuation coefficient $\alpha$ was taken to vary as frequency to the $n^{th}$ power, $$\gamma = \alpha + j\beta = \alpha_o\left(\frac{f}{f_o}\right)^n + \frac{j\omega}{v} \quad (31)$$

where $n \approx 1.5$. For electrical loss the complex dielectric constant was defined as $$\varepsilon_{33}^s = \varepsilon_r\varepsilon_o(1 - j\tan(\delta_e)) \quad (32)$$

where $\delta_e$ is the dielectric loss tangent of the material, $\varepsilon_r$ is the relative dielectric constant.

To compute the electrical impedance of system comprising a single piezoelectric element, the loading impedances on each face of the transducer ($Z_L$, $Z_R$) must be calculated for the composite layers. This expression for successively transforming impedances layer by layer is given by $$Z^+ = Z_{in}\frac{Z_{Load}\cosh(\gamma d) + Z_{in}\sinh(\gamma d)}{Z_{in}\cosh(\gamma d) + Z_{Load}\sinh(\gamma d)} \quad (33)$$

where $Z_{Load}$ is the impedance of the loading layer and $Z_{in}$ is the impedance of the intermediate layer. The layer impedances are a function of frequency and are computed as $$Z(\omega) = \frac{j\omega\rho}{\gamma} \quad (34)$$

Another useful set of relations are the acoustic velocities at the faces of the transducer which are given by $$v_L = \left[\frac{h}{j\omega A}\frac{Z_o(1 - \cosh(\gamma a)) - Z_R\sinh(\gamma a)}{(Z_L Z_R + Z_o^2)\sinh(\gamma a) + Z_o(Z_L + Z_R)\cosh(\gamma a)}\right]\frac{V}{Z_e} \quad (35)$$

$$v_R = \left[\frac{-h}{j\omega A}\frac{Z_o(1 - \cosh(\gamma a)) - Z_L\sinh(\gamma a)}{(Z_L Z_R + Z_o^2)\sinh(\gamma a) + Z_o(Z_L + Z_R)\cosh(\gamma a)}\right]\frac{V}{Z_e}$$

By knowing the acoustic impedances loading each face of the transducer, the total radiated power can be calculated using $$P_{total} = P_L + P_{R=A/2}[\text{Re}(Z_L)|v_L|^2 + \text{Re}(Z_R)|v_R|^2] \quad (36)$$

For the subsequent 3D FEM analysis the amount of energy converted into heat is required for the boundary condition between the transducer and silver epoxy/aluminum heat sink. To compute this value, it is assumed that electrical and mechanical phenomena are the dominant loss mechanisms. From conservation of energy, $$P_m + P_e = \frac{1}{2}\text{Re}(Z_e)|I|^2 - P_{total\,Pe} = \frac{1}{2}R_p|I|^2 \quad (37)$$

where $P_m$ and $P_e$ are the mechanical and electrical loss in watts. $R_p$ is the combined internal electrical losses which is the real value of the electrical impedance at the frequency where the displacements are 0.

The solving procedure requires that the velocities, thicknesses, densities and attenuations are known for each layer. First, the propagation constant ($\gamma_n$) for each layer can be computed followed by computing Eq. (34) for each layer. Using Eq. (33), the impedance loading the transducer can be computed by successive substitution and combined with Eq. (30) to compute the total electrical impedance of the loaded transducer. The advantage of one-dimensional transmission line models is that they permit rapid design and optimization of transducers that have a large number of layers. Moreover, optimization algorithms can be used to enhance power output, impedance matching, and frequency response.

1D Transmission Line Model Analysis of BAW Transducer Array

For cell lysis, the BAW transducer must couple sufficient acoustic energy into a fluid-filled region to disrupt the cellular membrane. Preferably, the BAW transducer array also reversibly couples to a microfluidic cartridge to enable reuse of the transducer assembly while permitting disposal of the contaminated fluidic cartridges. Therefore, the design of the interface boundary between the acoustic transducers and the microfluidic channel is important to obtain the best possible acoustic coupling and permit reusability of the transducer array. Modeling can be used to investigate the physical parameters to reduce acoustic loss through the boundaries while permitting fluid movement through the microchannels. The modeled geometries of the unloaded and loaded transducer are shown in FIGS. 4a and 4b.

Figure 6:
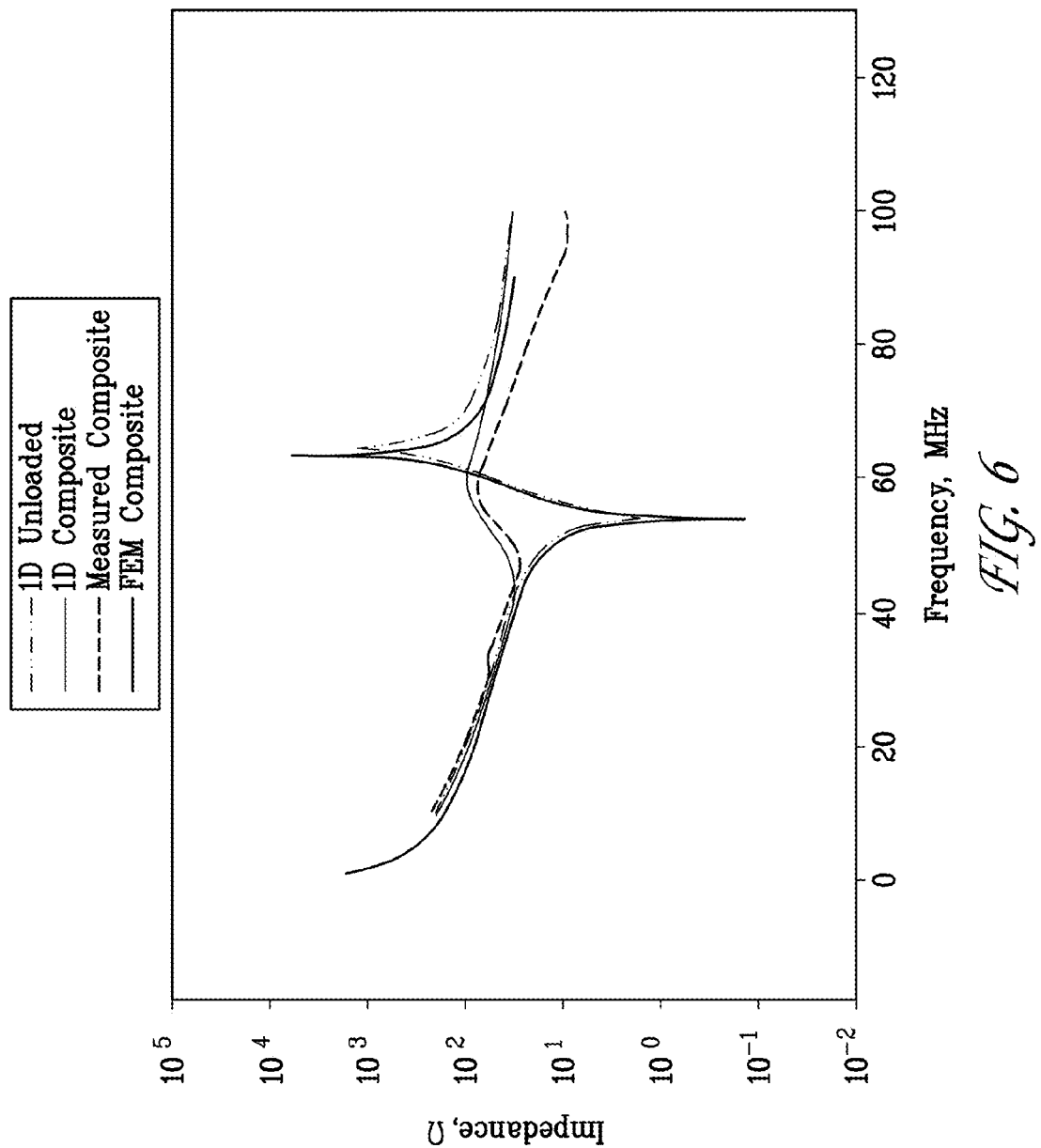
FIG. 6 is a graph of the impedance response of an unloaded and composite 36° Y lithium niobate transducer calculated using a 1D transmission line model.

The impedance response is shown in FIG. 6 for the unloaded and loaded 36° Y lithium niobate transducer based on the 1D transmission line and 2D FEM model. Though the unloaded transducer exhibits excellent resonance near 55 MHz, the impedance was a not optimal Z (55 MHz)=1.10−j7.15Ω. For the composite transducer, Z (55 MHz)=44.67−j16.9Ω), which a much better match to a 50 ohm system. Perfect matching requires exquisite tracking of the maximal drive frequency. Therefore, broadband behavior is preferable.

Figure 7:
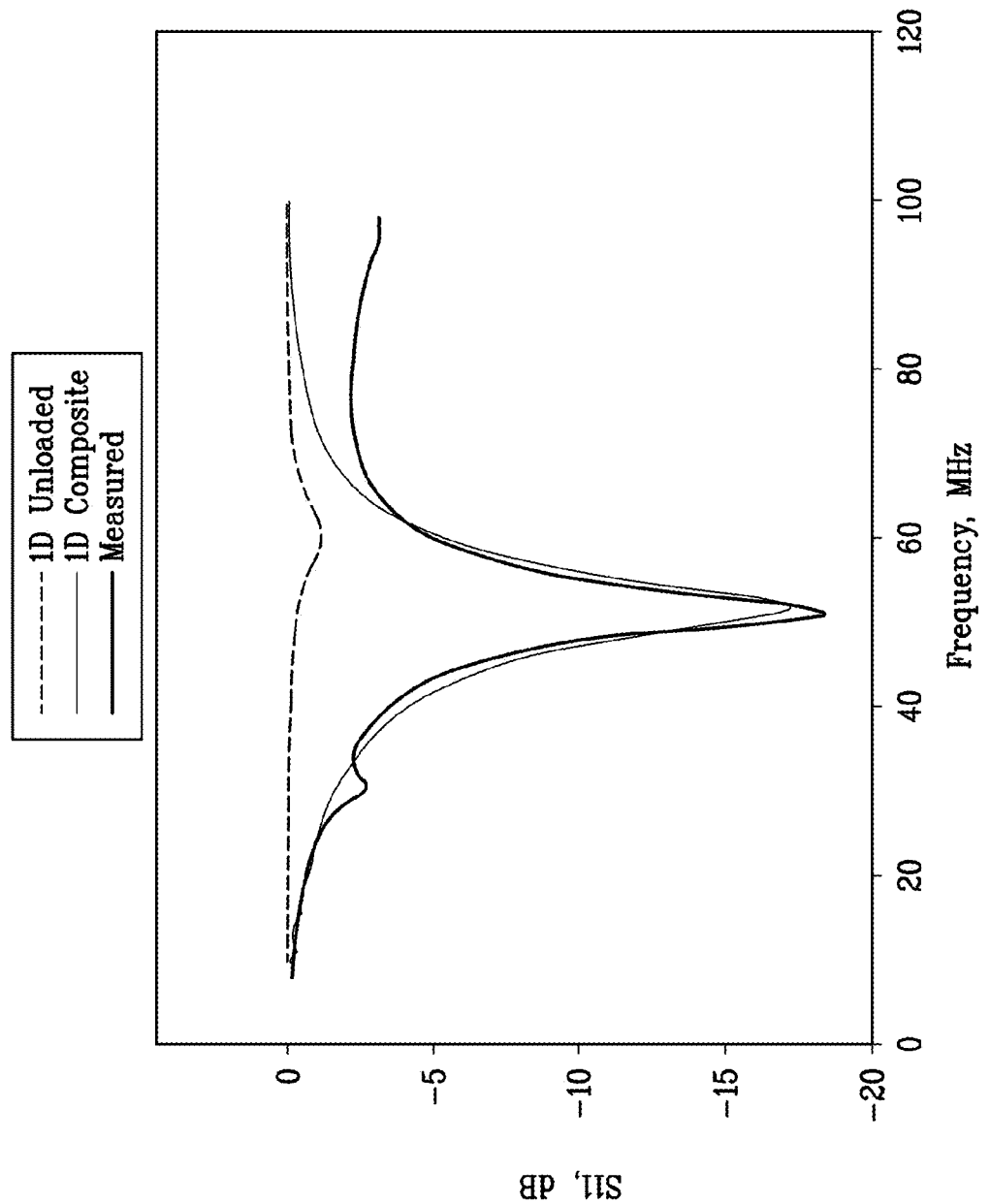
FIG. 7 is a graph of return loss (S11) for the unloaded and composite transducers based on 1D transmission line models.

Transmission line models are significantly faster computationally, providing rapid insight into the impact of various layers on the transducer. One disadvantage of this method is the cross-sectional area is assumed to be a constant from layer to layer. Despite the limitations of a 1D analysis, several key parameters can be extracted from this model: the return loss (S11), the acoustic velocities at the transducer faces, and the radiated acoustic power. FIG. 7 shows the return loss (S11) for the unloaded and composite transducers based on a 1D transmission line model. After proper layer-to-layer matching the return loss at the resonance frequency provides an excellent match to a 50 ohm source. The return loss for the composite transducer shown in FIG. 4b was −14.5 dB with a tunable range of 8 MHz based on maintaining 90% input power coupling to the transducers.

The 1D model can be used to compute the acoustic velocities at the faces of the composite transducer. For a peak-to-peak (P-P) input voltage of 2.78 V the acoustic velocities at both faces was computed with Eq. (35) to be 3.4 cm/sec at 54 MHz. The radiated acoustic power from the transducer was computed by applying Eq. (36) and using the loaded impedances and velocities at the transducer faces. At 54 MHz the total radiated acoustic power was 81.5 mW.

FEM Analysis of BAW Transducer Array

Impedance of Transducer and Composite Structure

Figure 8:
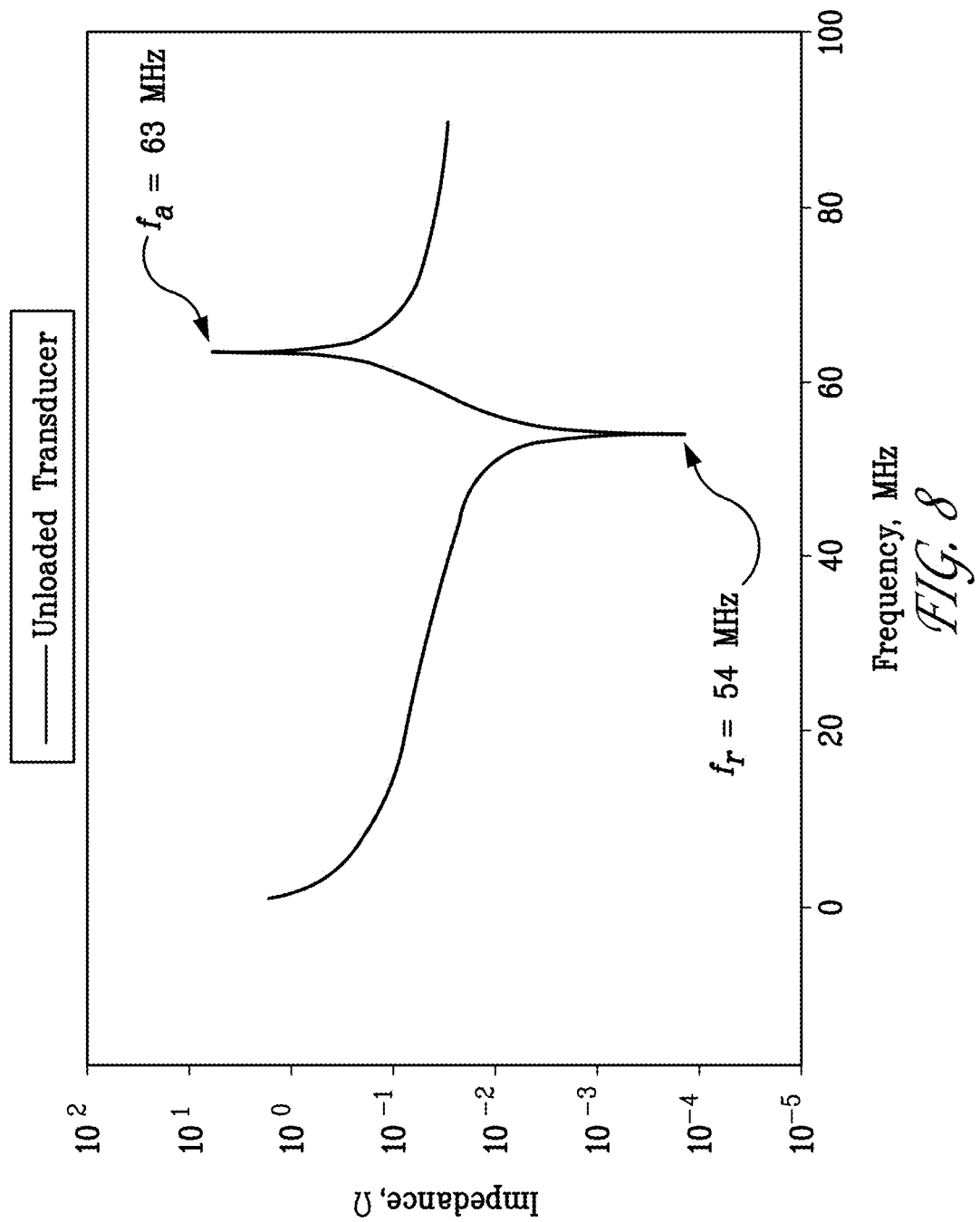
FIG. 8 is a graph of the extracted impedance response of 36° Y lithium niobate transducer based on a 2D FEM.

A more realistic model can be developed using a 2D FEM and 2D axially symmetric analysis which correctly accounts for changes in area from layer to layer. To compute the impedance of the transducer, a known voltage was applied to the driven electrode and then the induced surface charge was computed. By sweeping the frequency, the impedance was calculated using Eq. (12). The calculation was based on 2D FEM of the transducer with infinitesimally thin Au electrodes in air. FIG. 8 shows extracted impedance response of 36° Y lithium niobate transducer from a 2D FEM. The resonance and anti-resonance frequencies, assuming lossless conditions, can be used to compute the piezoelectric coupling constant K. The piezoelectric coupling coefficient was computed from the known material parameters as defined in Table I and compared with the extracted K from the FEM impedance data. The materials parameters gave $K_{33}$=54% which agreed well with $K_{33(FEM)}$=56.1% from the FEM model. This indicates that the 2D FEM model parameters are suitable for building more complex models of the acoustic transducer.

Acoustic Pressure in the Microchannel

Figure 9A:
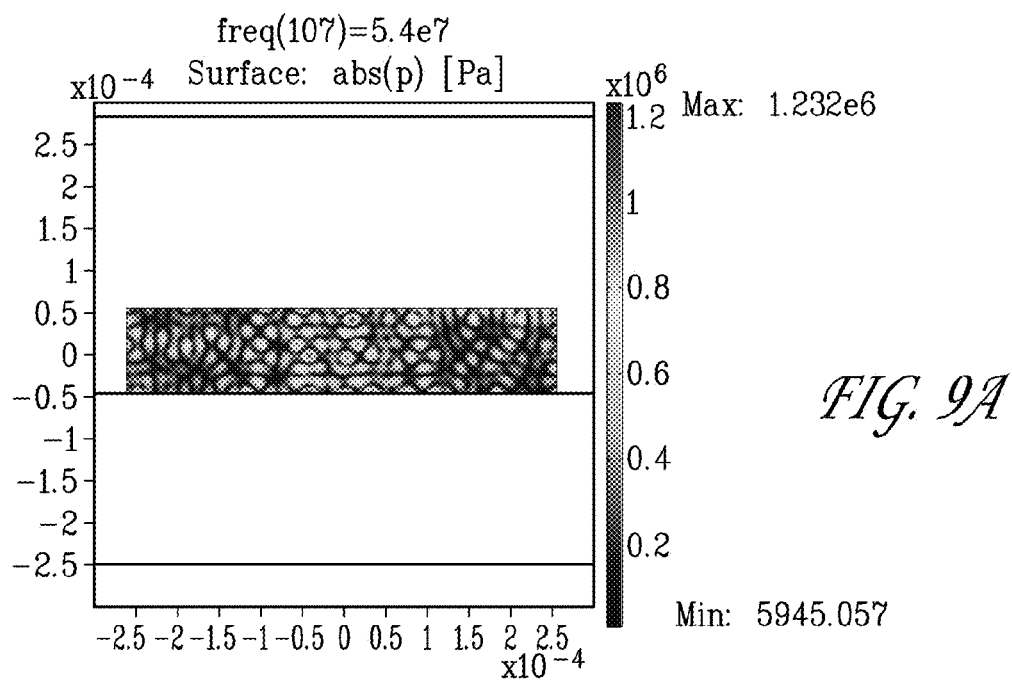
FIG. 9a is a plot of the acoustic pressure within the channel cross-section at 54 MHz.
Figure 9B:
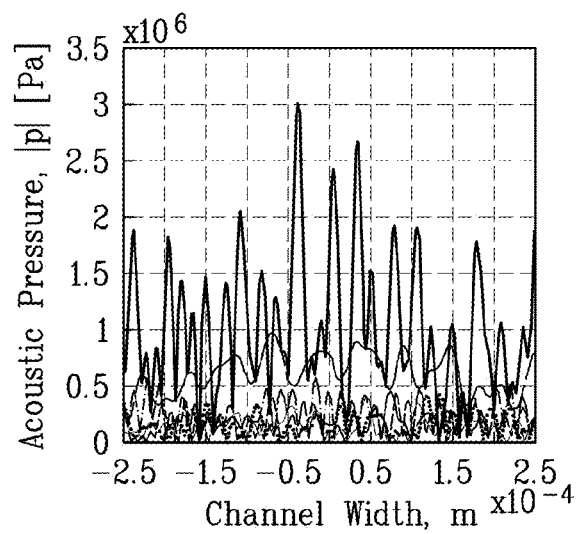
FIG. 9b is a plot of the acoustic pressure at several drive frequencies across the width of the channel.
Figure 9C:
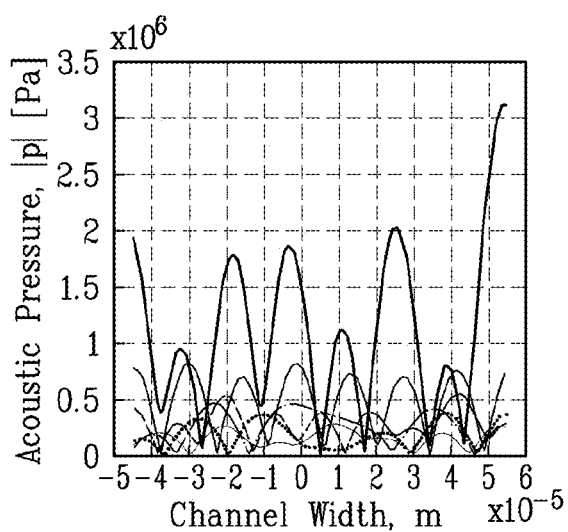
FIG. 9c is a plot of the acoustic pressure at several drive frequencies across the height of the channel.

A 2D FEM model was used to compute the acoustic pressure distribution within the fluid region suitable for cell lys-ing. This fluid region was modeled as a cross-section of the channel. Since the acoustic fields are nearly instantaneous compared to the mass transport through the microchannel, a 2D simulation was sufficient to capture the pressure field. FIG. 9 shows the localized acoustic pressure within the channel cross-section. FIG. 9a shows the acoustic pressure at 54 MHz for an applied voltage of 3 $V_{P-P}$ across the transducer. The resulting peak acoustic field was ~1 MPa with portions of the microchannel around 0.2 MPa. The acoustic pressure was computed at several drive frequencies across both the width and the height of the channel along cross-sectional lines through the center of the channel, as shown in FIGS. 9b and 9c. FIG. 9b shows the acoustic pressure at several drive frequencies across the width of the channel. FIG. 9c shows the acoustic pressure at several drive frequencies across the height of the channel. The acoustic pressure was maximized and the optimal coupling to the frequency source was matched at 54 MHz. The BAW transducer had 90% electrical power coupling efficiency across a bandwidth of 8 MHz, which provided excellent operating range. The acoustic pressure profiles within the microchannel demonstrate the scale at which the pressure undergoes rapid changes was on the order of 20 μm.

Energy from Acoustic Fields in Microchannel

Figure 10:
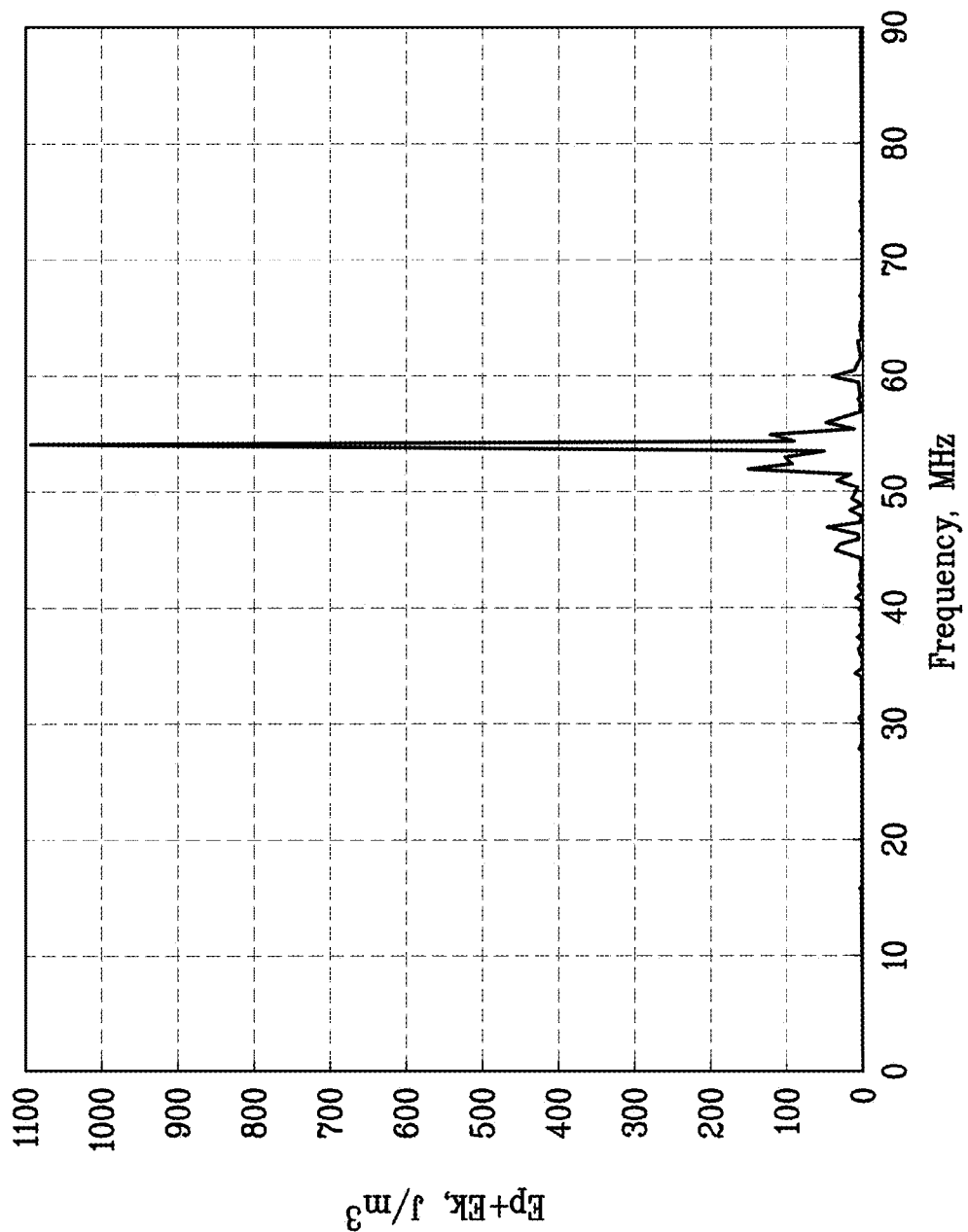
FIG. 10 is a graph of the kinetic and potential energy of the acoustic fields in the center of microchannel.

The energy of the acoustic fields can be calculated as a function of the drive frequency. This can be used to determine if other possible acoustic modes are leaking energy from the primary excitation frequency. Using Eq. (16), the kinetic and potential energy due to the pressure and velocity of the acoustic waves were computed versus the drive frequency. FIG. 10 shows the kinetic and potential energy of the acoustic fields in the center of channel. This computation indicates that the primary BAW mode is being excited and converted to acoustic energy at 54 MHz.

Thermal Analysis

The thermal variation from the inlet to the outlet of the microchannel can be calculated from heat flux entering the boundary between the transducer and epoxy layers. This heat flux is the result of electrical and mechanical losses with the transducer. By using heat flux discontinuities at these boundaries, the computation can be simplified from a time-dependent to steady state model. This is a valid assumption when the lysing time is sufficiently long (e.g., 20 seconds) and, therefore, nearly reaches the steady state. First, the P-P voltage delivered to each BAW transducer at 50Ω) was computed as 2.78 V-3.47 V which corresponded to the known input power (i.e., 21.9-23.8 dBm). Then the 1D transmission line model was used to compute the radiated power of the emitted acoustic waves. By knowing the applied power input, conservation of energy can be applied (Eq. 37) to determine the mechanical and electrical loss. Since the transducer is most efficient at 52-54 MHz, the radiated acoustic power was taken at this frequency. These values were used in the 1D model to determine the radiated acoustic power, mechanical and electrical losses. Using Eqs. (36) and (37), the combined loss from the mechanical and electrical processes was 11.1 mW with a radiated acoustic power of 81.5 mW. The electrical loss ($P_e$) was only 0.7 mW. The power density across the transducer was 1570 W/m² for a delivered power input of 21.9 dBm.

TABLE II

Electrical Power delivered to BAW Transducers and Resultant Input Power Density

| Delivered Power[1] (dBm) | Equivalent Power (mW) | Induced P – P Voltage for 50 Ω load (V) | $P_e + P_m$ (mW) | Power Density due to losses (W/m²) |
|---|---|---|---|---|
| 21.9 | 154.4 | 2.78 | 11.1 | 1570.3 |
| 22.8 | 192.9 | 3.11 | 13.9 | 1966.4 |
| 23.8 | 241.1 | 3.47 | 17.3 | 2447.4 |

[1]Delivered power is the electrical power received by the transducer as if it was perfectly matched.

A 3D thermal model was used to model the physical boundary conditions and operation of the actual device shown in FIGS. 1 and 4b. To represent the operation of the acoustic transducers, the interface between the acoustic transducers and the conductive epoxy were modeled as heat flux discontinuities. This model was solved for the steady state condition. At this boundary heat enters the system from acoustic mechanical and electrical losses ($P_m + P_e = 1570$ W/m²). This is a reasonable approximation since the heat source is strictly a result of the losses in the system and eliminates the need to compute time dependent problems. At a power input of 23.8 dBm, significant heating was observed at the microchannel outlet for the lower flow rates (i.e., 5-30 µl/min).

Figure 11:
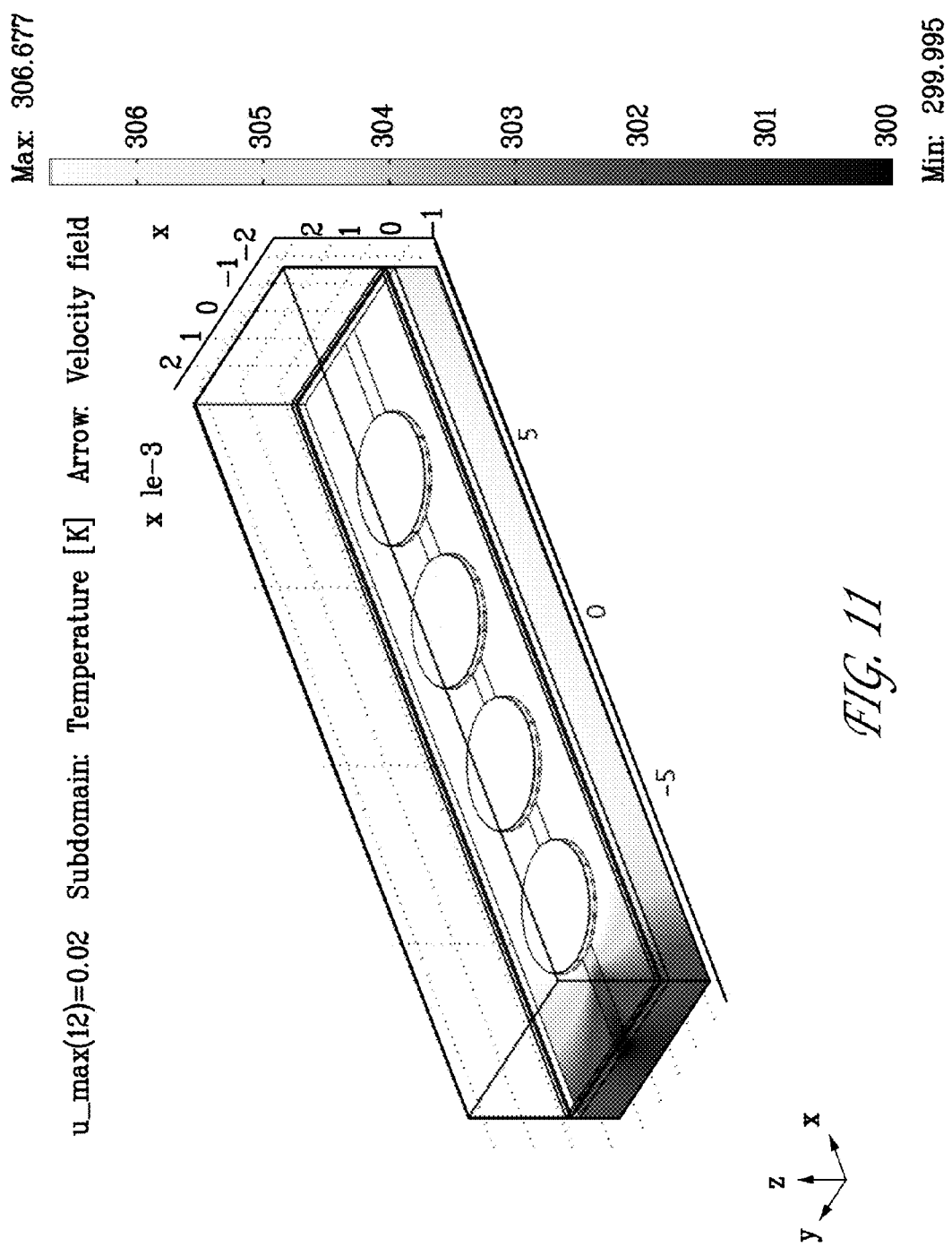
FIG. 11 shows a 3D thermal model of BAW lysing device.

FIG. 11 shows the 3D thermal model of the BAW transducer array and microchannel. This analysis was done at 0.02 m/s, which corresponded to a 6 µl/min fluid flow in the channel. The channel inlet (lower left) starts at 300° K. and reaches a steady state value of 306° K at the outlet (upper right). The input power to each transducer was 21.9 dBm. Lysing results indicated that a power input of 21.9 dBm was more than sufficient to disrupt the cellular membranes at a flow rate of 40-50 µl/min.

Figure 12:
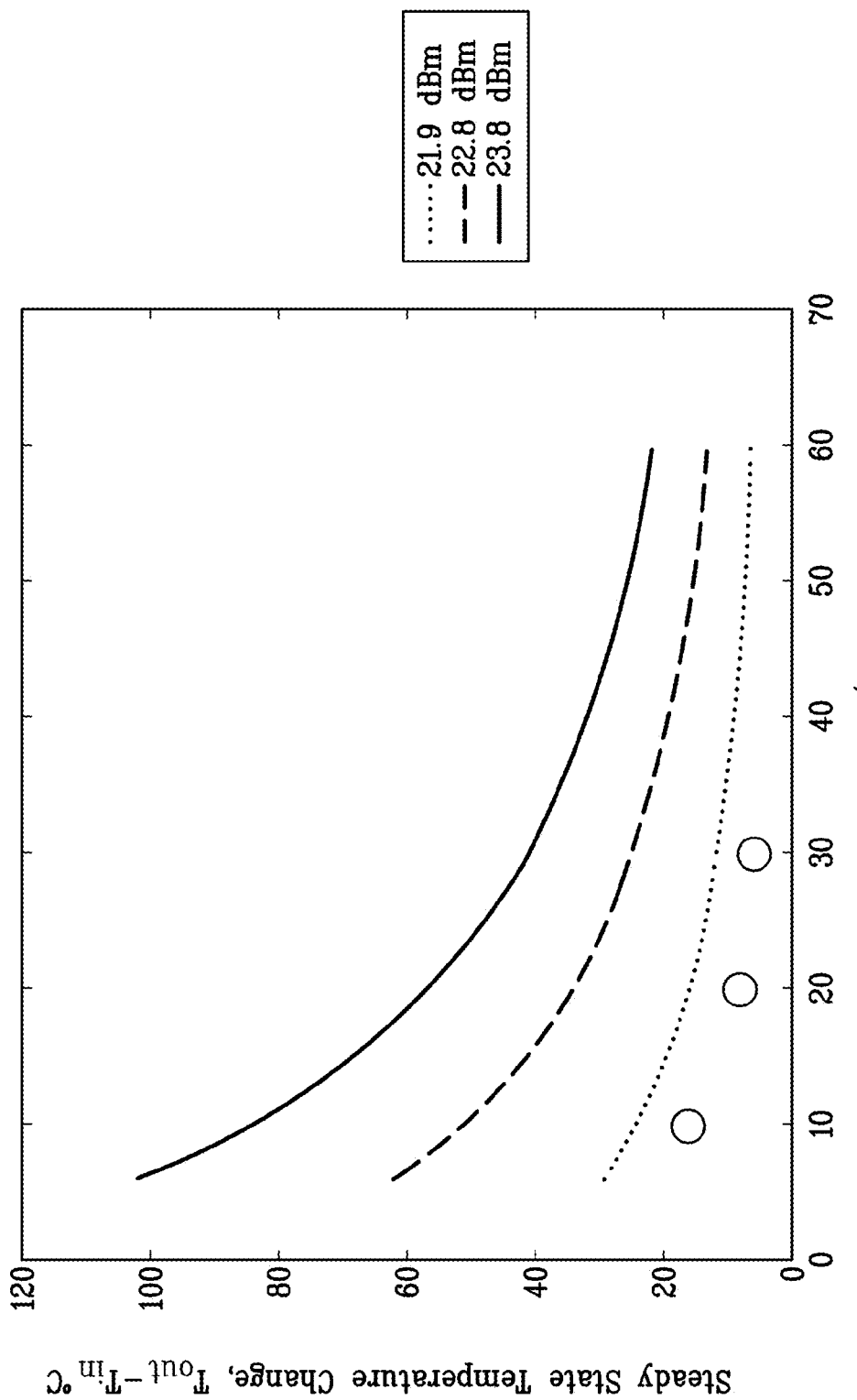
FIG. 12 is a graph of the steady state thermal response versus the input power to the BAW lysing device.

FIG. 12 shows the steady state thermal response versus the input power to the BAW transducer array. The open circles are the experimentally measured temperature near the channel outlet. The thermal results are for the steady state condition and therefore are slightly higher than for an actual lysing event. The experimentally measured temperatures were slightly less than the model due to thermal separation between the resistance temperature detector and the actual outlet.

Cavitation Threshold

Reducing the effects of cavitation is important to ensure optimal lysing efficiency within the microchannel. Though cavitation (i.e., rapid formation and collapse of bubbles within a fluid) may cause cell lysis, the formation of air bubbles within the microchannel dramatically reduces the flow rate. Previous calculations indicate that cavitation is frequency dependent with a threshold of ~$8 \times 10^5$ W/m² at 50 MHz. See V. R. Esche, *Acoustica* 2, pp. AB 208 (1952). Cavitation can occur in the fluid at a power density above this threshold. To compare with the actual device the cross-sectional area of the transducer was $\pi r^2 = \pi(1.5 \text{ mm})^2 = 7.1 \times 10^{-6}$ m². The power applied to each transducer was ≈143 mW, giving a total of $8.1 \times 10^4$ W/m², indicating operation was below the cavitation threshold. Cavitation was observed at the highest power setting of 23.8 dBm which corresponded to 241.1 mW delivered to each transducer or $1.3 \times 10^5$ W/m². This value was on the order of the reported cavitation threshold.

Experimental Demonstration of Cell Lysis

Cell Sample Preparation

*Escherichia coli* cultures were cultivated in a cation-adjusted broth, following standard methods. Organisms were incubated at 37° C. and 120 RPM in a shaking water bath, and growth was followed by monitoring the change in optical density of the suspension at 600 nm ($OD_{600}$) using a spectrophotometer. Cells were grown to log phase, harvested, washed twice in 1×PBS and resuspended in 1×PBS at an average cell density of $5 \times 10^8$ CFU/mL. The stock suspension was kept refrigerated and all experiments were completed within two hours of the initial sample preparation.

Sample Ultrasonication Using a Commercial System

Positive controls were performed using a 20 kHz bench top ultrasonication system, using both acoustic finger and acoustic cup configurations. For the acoustic finger experiments, a 1/16" tip was inserted into a 2 mL microcentrifuge tube containing a 1 mL sample using 12 W of applied power and an 8% duty cycle as recommended by the manufacturer (total process time=60 sec). During the experiment, the sample container was submerged in an ice bath to dissipate heat generated by the acoustic transducer. In the acoustic cup configuration, 100 µL of sample in a closed 2 mL microcentrifuge tube was submerged into a water-filled cup, the base of which encapsulated a 1.8" flat acoustic transducer. During the experiment, 58.5 W of power was applied at a 100% duty cycle (total process time=21.5 minutes). Heat generated by the transducer was dissipated by circulating the water through a chiller for the duration of the experiment. No mechanical or chemical lysing agents where added to improve lysing efficacy.

Sample Sonication Using the Microfluidic Lysing Device

Approximately 50 µL of cell suspension was loaded into a 1 cc syringe and injected into a microfluidic cartridge through a short length of 0.030 mm ID/0.065 mm OD flexible silicone tubing using a syringe pump. A second syringe pump was used to withdraw the sample from the channel through a second length of tubing. A synthesized signal generator and an RF power amplifier were used to drive the piezoelectric transducers for all experiments. Power input was varied from 0-200 mW at 100% duty cycle and sample flow rates were varied from 10-25 µL/min to maximize lysing efficiency while avoiding excessive heat generation and acoustic cavitation during the experiments. The microfluidic system was flushed with 0.5 mL distilled water between experiments. Additional flow-only experiments were performed to insure that cell lysis was not occurring through a shearing mechanism during the sample injection process.

Cell Viability

The efficacy of the sonication platforms was further measured by comparing viable cell counts before and after treatment using the method of Miles and Misra for plate counts. See A. A. Miles and S. S. Misra, *Journal of Hygiene* 38, 732 (1938). A serial 10-fold dilution of the sample was performed in sterile 1×PBS within ten minutes of the lysis experiments. Aliquots of 20 µL were spotted in triplicate onto a plate count agar and incubated at room temperature for 24 hours. The percentage of viable cells was calculated using 100($C_0 -$ $C_{treated}/C_0$, where $C_0$ is the average viable cell count prior to sonication and $C_{treated}$ is the average viable cell count after sonication.

Comparison of Commercial Ultrasonication and Microfluidic Lysing Devices

Figure 13:
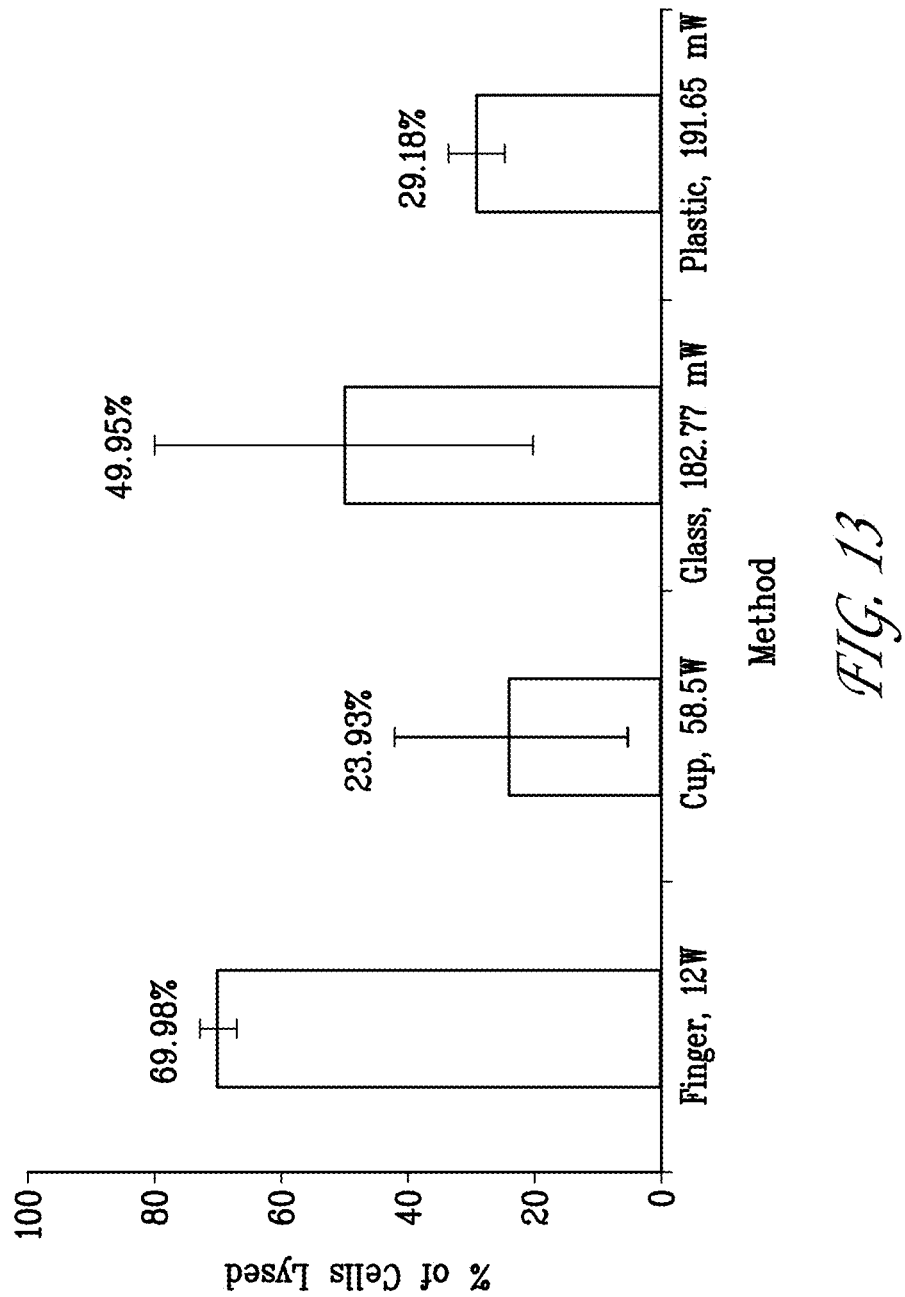
FIG. 13 shows a comparison of cell lysis efficiency for a commercial system and a microfluidic lysing device using a cell culture plating viability assay.

FIG. 13 shows a comparison of cell lysis efficiency for the commercial ultrasonication devices and the microfluidic cell lysing devices of the present invention. 'Glass' and 'Plastic' refer to the coupling layer between the transducer and microchannel. Glass is expected to be less acoustically lossy than plastic and hence improve cell lysis. The data for the two microfluidic systems were measured at 10 µL/min flow rates. The graph demonstrates that the lysing efficiency of a microfluidic lysing device is very competitive with the commercial ultrasonication system, and requires much lower power input (i.e., ~200 mW as compared to the commercial system operating at 12-58.5 W). The performance gain of the microfluidic lysing device can be attributed to the operating frequency and hence the wavelength of the propagating acoustic waves in the fluid. For maximum transfer of acoustic energy to the biological cells, the acoustic wavelength, λ, can be comparable to the size of the cell, which in the case of E. coli, is ~2 µm. Given the speed of sound, v, in water is ~1500 m/s, the relationship λ=v/f can be used to predict the wavelength of the acoustic pressure wave for the commercial and BAW devices. At an operating frequency, f=20 kHz, the acoustic wavelength of the commercial system was 75 mm, while the wavelength of the 54 MHz BAW transducer array was 27.8 µm, allowing for efficient energy coupling to the cells. The error bars at each data point indicate that, for some experiments, there was large variation in viable cell counts. This effect was caused by the number of serial dilutions that were required to obtain appropriate plate counts, resulting in a $10^5$ dilution factor that amplified small variations in counting.

Figure 14A:
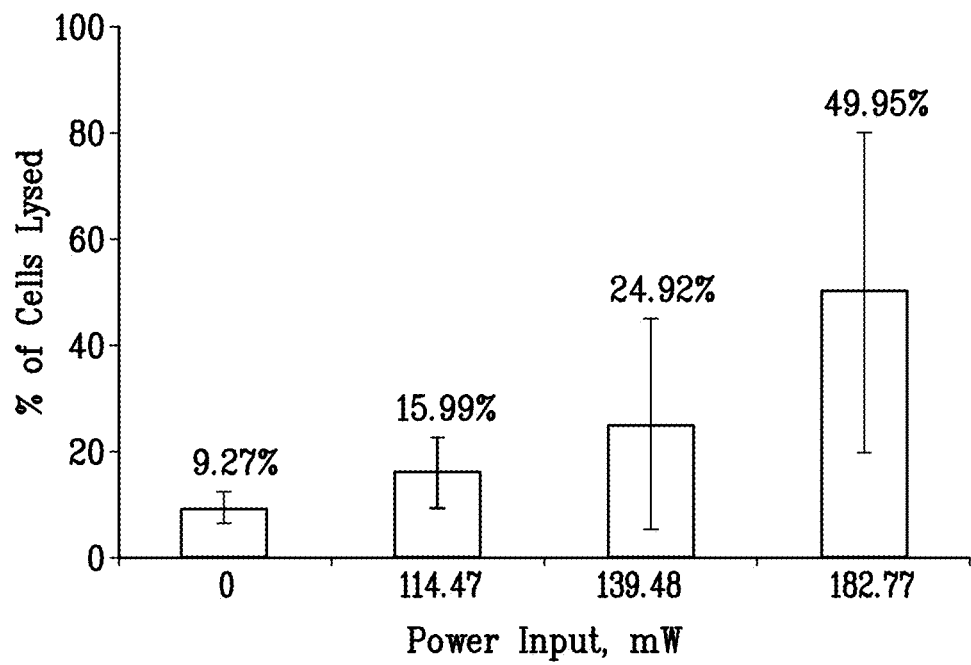
FIG. 14 shows cell lysis efficiency the microfluidic lysing device versus input power for a) glass substrate and b) plastic substrate.
Figure 14B:
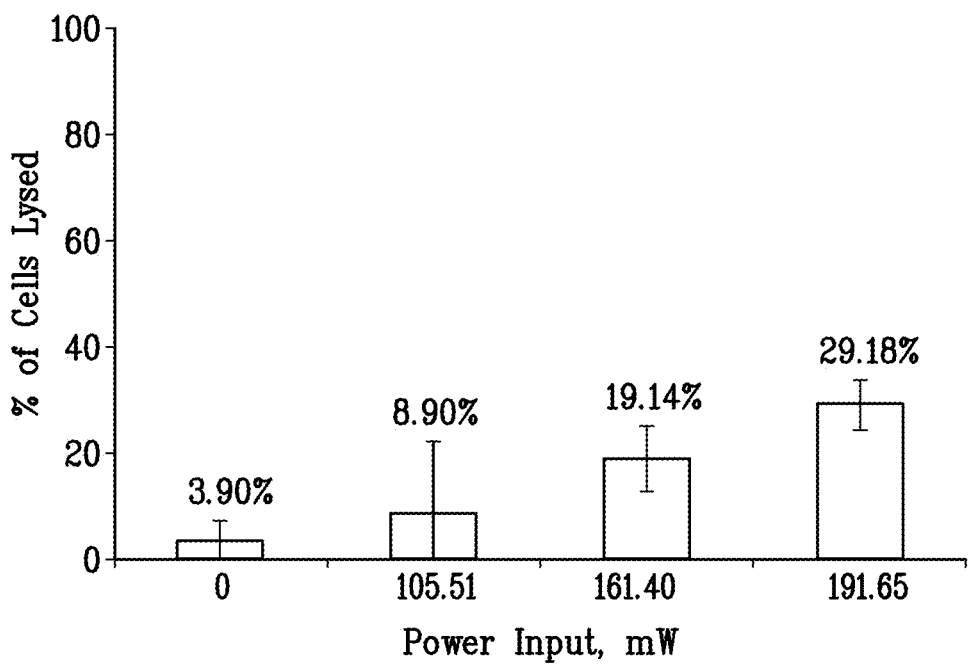

FIG. 14 shows graphs of the cell lysis efficiency the microfluidic lysing device versus input power delivered to the transducer. FIG. 14a shows the cell lysis efficiency for a glass coupling layer. FIG. 14b shows the cell lysis efficiency for a plastic base. The flow rate was 10 µL/min for both bases. Cell lysis efficiency was 5-20% higher for microfluidic cartridges with glass interfaces as compared to cartridges with plastic interfaces. This result was expected since glass has very low acoustic loss as compared to plastic. However, this result demonstrates that ability to lyse cells using a completely plastic microchannel, which substantially simplifies fabrication complexity and cost. Further, a serpentine channel can be used to increase the exposure time to the acoustic pressure field. The additional path length provides an additional tuning parameter between lysis efficiency and the subsequent nucleic acid extraction. Power can be increased to improve lysis efficiency, while not generating excess heat by the transducer according the thermal analysis.

Nucleic Acid Extraction from the Lysate

The microfluidic cartridge can also provide the necessary fluidics to mix the lysate in a downstream nucleic acid extraction portion. Preferably, the extraction method can be integrated with a microfluidic cartridge, is compatible the fluidic requirements for interfacing with the cell lysis portion, and enables fast extraction time on the scale of a few minutes. FIG. 15 shows exemplary nucleic acid extraction methods that can be integrated with cell lysis in a microfluidic cartridge. FIG. 16 shows top-view schematic illustrations of exemplary implementations of the cell lysis and the nucleic acid extraction portions in microfluidic cartridges. The microfluidic cartridges in FIG. 15 can be reversibly coupled to a BAW transducer array similar to that shown in FIG. 2.

Sol-Gel Packed Microchannels

FIG. 15a shows a method for nucleic acid extraction using a sol-gel silica bead matrix. See Wolfe et al.; and Cady et al. First, lysate is introduced into the silica bead matrix, resulting in selective absorption of nucleic acid on the silica beads through an electrostatic interaction. The beads can then be rinsed to remove contaminants and excess lysate. Finally, the absorbed nucleic acid can eluted from the bead matrix with a suitable buffer.

Figure 16A:
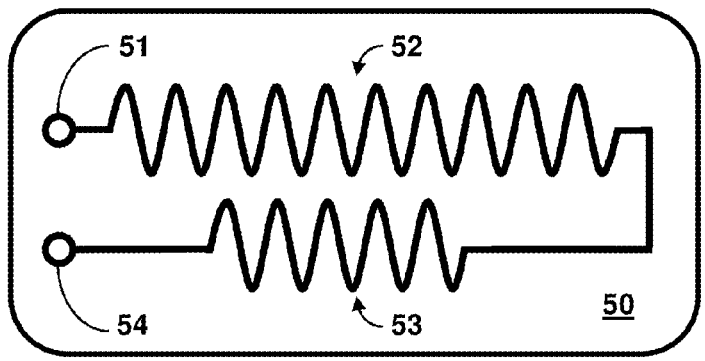
FIG. 16 is a graph of DNA extraction profile and cumulative extraction of DNA from a packed bed sol-gel silica bed matrix extraction device as a function of collected fraction.

FIG. 16a shows top-view schematic illustration of an implementation of microfluidic cell lysis and sol-gel/silica bead matrix extraction in a microfluidic cartridge 50. Whole cells in solution can enter the microfluidic channel through a cell inlet 51 and be acoustically lysed in a lysis portion 52. An acoustic transducer array (not shown) disposed on the channel couples acoustic energy into the lysis portion 52 of the cartridge 50, causing the whole cells to lyse therein by localized acoustic pressure. As shown, a serpentine channel can be used to increase the exposure time to the acoustic pressure field in the lysis portion 52. Lysate then flows out of the lysis portion 52 and into the nucleic acid extraction portion 53, comprising the sol-gel silica bead matrix. Nucleic acid is selectively absorbed on the silica beads in the nucleic acid extraction portion 53. Subsequent steps can include rinsing of the beads and elution of the absorbed nucleic acid. In each step, excess lysate or eluted nucleic acid can exit the channel through an outlet 54.

The silica matrix can be fabricated by injecting or patterning a sol-gel matrix containing silica beads in the microchannel. Sol-gel and silica bead matrices bind DNA/RNA to their matrices through an electrostatic interaction. The silica beads provide a large surface area for selective binding of DNA, while the sol-gel serves as a silica-based glue to hold beads in place during device operation. As an example, DNA extraction microchannels were fabricated using wet etching of serpentine channels in borosilicate glass substrates. A sol-gel silica bead matrix was introduced into the microchannels by injection into a closed microchannel. Tetraethyl orthosilicate (TEOS) based sol-gel and beads (15 µm diameter silica) were mixed at a concentration of 200 mg of beads in 1 ml of sol-gel. The chamber outlet was plugged ~90% to allow some fluid to exit, but confine a substantial amount of beads in the channel. The sol-gel-bead matrix was injected into the microchannel under pressure (or vacuum) to achieve high density packing. After filling, the chamber was dried at 120° C. for 24 hours to lock the beads in place. Alternatively, the DNA extraction matrix can be sprayed into an open microchannel having a coverslip removed. The aerosol spray method can produce reliable, high surface area sol-gel matrices, with controllable pore sizes. A high surface area was advantageous for maximizing DNA extraction from a sample.

Figure 17:
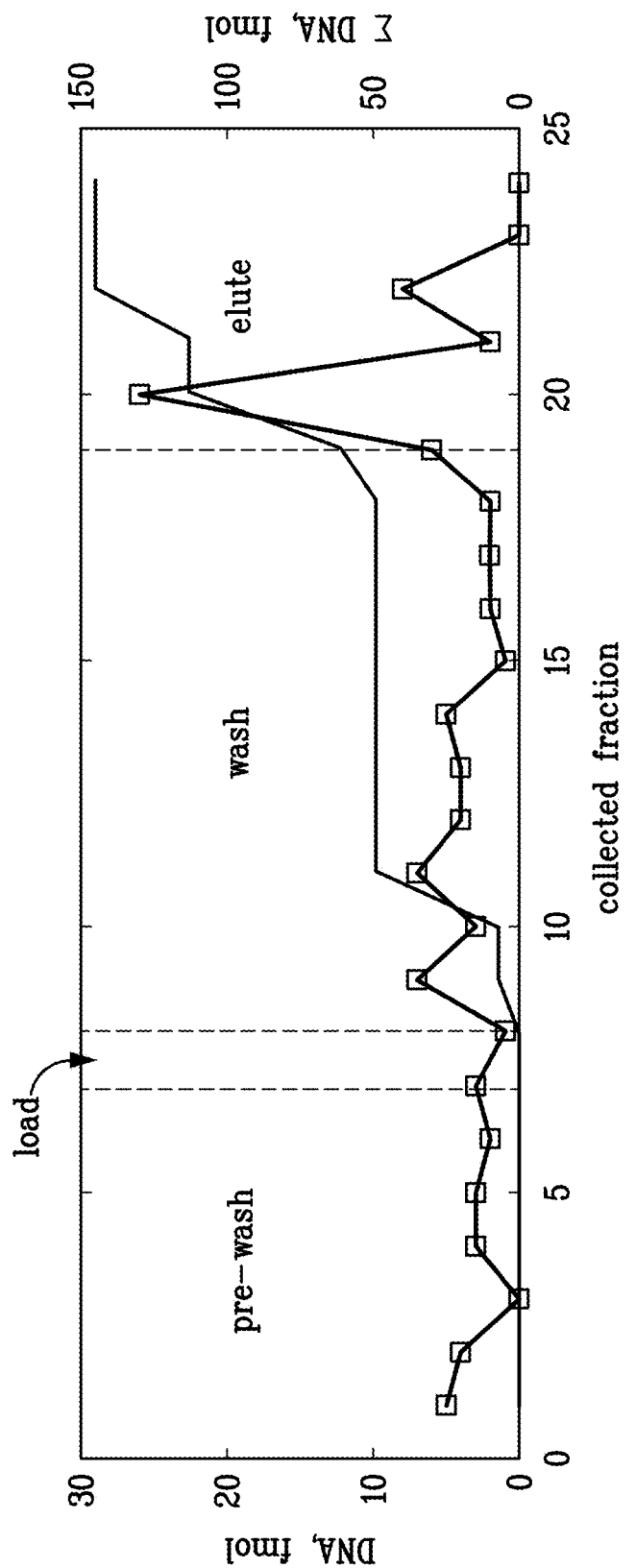
FIG. 17 shows Mass of DNA extracted using ChargeSwitch® beads with microfluidic cartridge designs 1 and 2 and a sample flow rate of 10 µL/min.

Samples of DNA were extracted from a sample solution containing 250 fmol of DNA. The extraction microchannel comprised a 10-20 mm long packed bed in a 150 µm wide, 150 µm high, and 332 mm long channel. The DNA bound to the silica matrix, allowed excess lysate (e.g., proteins) to pass through as waste. As shown in FIG. 17, fractions were collected during the entire process to isolate the DNA from excess lysate. The extraction efficiency was 40%.

DNA Binding to Paramagnetic Beads

FIG. 15b shows a method for nucleic acid extraction using paramagnetic beads. Nucleic acid binding magnetic beads can be mixed with the lysate, resulting in selective absorption of nucleic acid on the functionalized magnetic beads. The bound magnetic beads can be immobilized to a surface using magnetics (e.g., NdFeB). The immobilized bound magnetic beads can then be rinsed to remove contaminants and excess lysate. A pH shift from 6.5 to 8.5 can then be used to elute the purified nucleic acid from the immobilized beads.

Figure 16B:
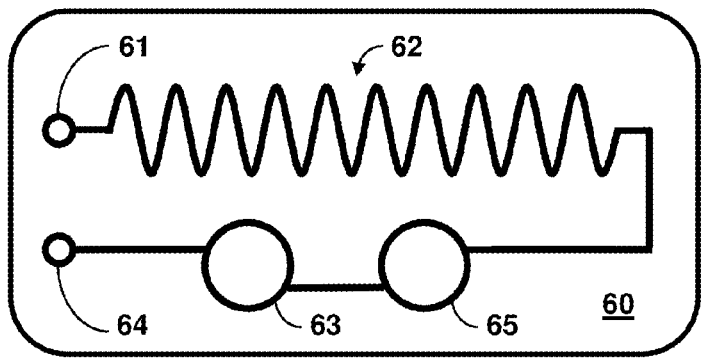

FIG. 16b shows a top-view schematic illustration of an implementation of microfluidic cell lysis and magnetic bead-based nucleic acid extraction in a microfluidic cartridge 60. Whole cells can be mixed with nucleic acid binding magnetic beads (e.g., $10^6$ beads/ml) in a solution that can enter the microfluidic channel through an inlet 61. The cells can be acoustically lysed in a lysis portion 62. An array of acoustic transducers (not shown) disposed on the channel couples acoustic energy into the lysis portion 62, causing the whole cells to lyse therein by localized acoustic pressure. As shown, a serpentine channel can be used to increase the exposure time to the acoustic pressure field in the lysis portion 62. DNA in the lysate will selectively bind to the magnetic beads. Lysate and the bound beads then flow out of the lysis portion 62 into the nucleic acid extraction portion 63, comprising a magnetic trap for immobilization of the magnetic beads therein. One or more magnets (not shown) disposed proximate the trap can be used to immobilize the beads to a surface of the trap. Subsequent steps can include rinsing of the beads and elution of the absorbed nucleic acid. In each step, excess lysate or eluted nucleic acid can exit the channel through an outlet 64. The channel can further comprise a mixing chamber 65. A piezoelectric transducer can be disposed proximate the mixing chamber 65 for active mixing of the beads with reagent solution and to acoustically drive DNA off of the bead surface. Nucleic acid is selectively absorbed on the silica beads in the nucleic acid extraction portion 63.

Several commercially available kits employ silica or polystyrene beads with a paramagnetic core for rapid, facile isolation of DNA from a complex mixture of cellular lysate. For example, the ChargeSwitch® gDNA Mini Bacteria Kit manufactured by Invitrogen reversibly binds DNA to the bead surface in response to a change in solution pH. Following cell lysis, DNA is bound to the surface of the 1 μm ChargeSwitch® magnetic beads by lowering the solution pH to <6.5, which protonates the bead surface for binding with the negatively charged phosphate backbone of the DNA. Unbound contaminants are removed in two wash steps, and the DNA is eluted from the beads by raising the pH to 8.5, which deprotonates the bead surface and releases the bound DNA. The paramagnetic core of the beads permits immobilization of the beads within an externally applied magnetic field for reagent exchange without sample loss. These kits provide a method for performing high-throughput assays in a reduced volume that is suitable for translation into a microfluidic chip-based format.

A cartridge was fabricated to test the recovery of genomic E. coli DNA, strain B following the bead-based assay. Modifications to the basic lysis cartridge presented in the previous section were made to integrate ChargeSwitch® beads for DNA extraction and purification following acoustic lysis. The acoustic portion of the cartridge lysed the cellular samples and immediately captured nucleic acid to the surface of magnetic beads. The magnetic core of the beads allowed confinement within the extraction portion of the microchannel as the buffer was exchanged to remove non-nucleic material. Two removable ¼" diameter magnets were employed for selective trapping of beads within the channel during the assay. Passive binding and release of DNA occurred as the reagent solutions were passed over the bead reservoir. Alternatively, a piezoelectric transducer can be positioned under the bead reservoir for active mixing of the beads with the reagent solution and to acoustically drive DNA off of the bead surface. Approximately $1\times10^6$ beads were loaded into the channel for DNA extraction. Assays buffers consisted of a "binding buffer" (pH<6.5), a "wash buffer" (pH=7.0), and an "elution buffer" (pH=8.5). For each experiment, 100 μL of genomic E. coli DNA solution was combined with 300 μL of binding buffer and injected into the microfluidic cartridge, followed by 500 μL of wash buffer to remove nonspecifically bound impurities. In the last step, 200 μL of elution buffer was injected to release bound DNA. The eluent from each step was collected and analyzed for DNA content using a dye that fluoresces upon binding with double-stranded DNA.

Figure 18:
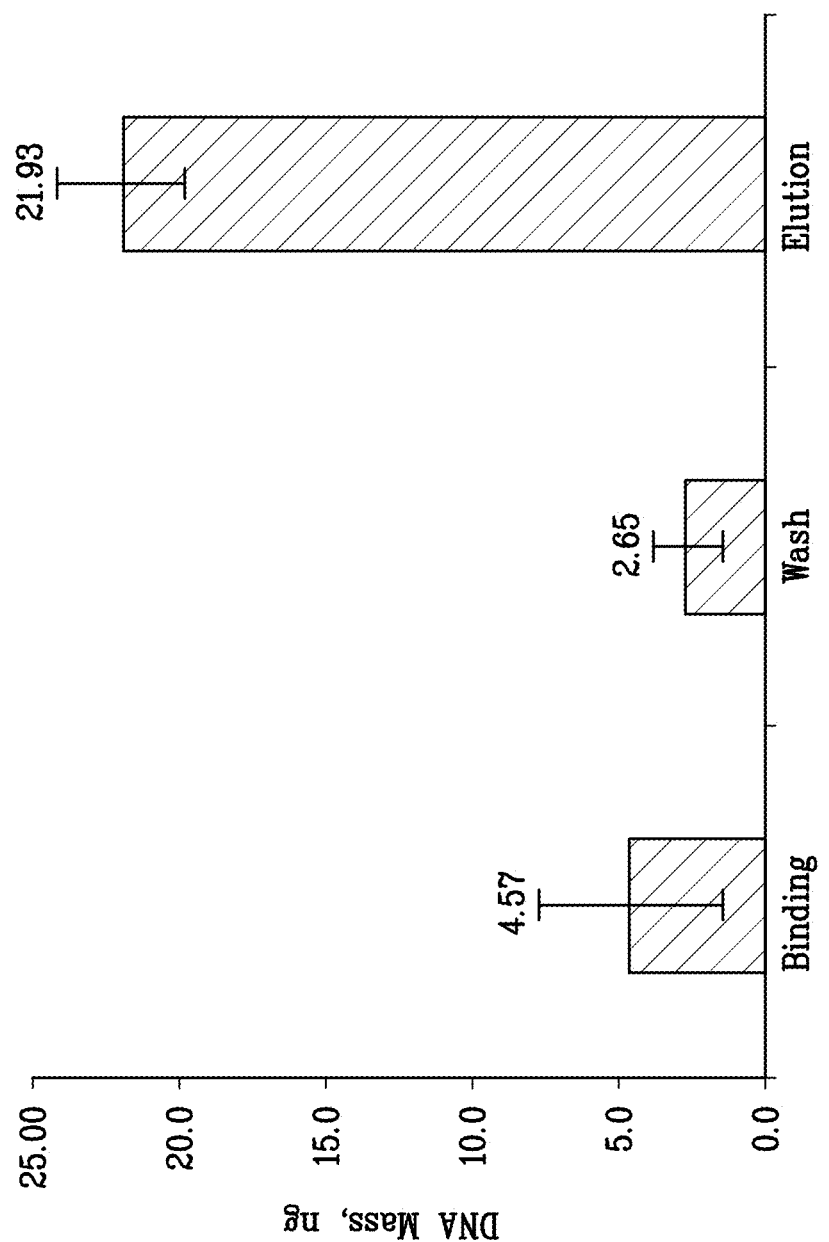
FIG. 18 shows Mass of DNA extracted using ChargeSwitch® beads with microfluidic cartridge design 3 and a sample flow rate of 50 µL/min.

FIG. 18 shows the DNA extraction performance of the ChargeSwitch® beads when 201 ng of DNA was loaded into the channel. 21.93 ng DNA (about 20%) was recovered in elution. DNA also appears to be more efficiently bound during the binding step with less non-specifically bound DNA being removed during the wash step. A significant portion of the unrecovered DNA may have bound nonspecifically along the channel interior. Given that the cartridges were fabricated in plastic, the intrinsic surface charge may have bound DNA and caused additional sample loss. One method to mediate this effect is to passivate the microchannel to reduce the surface charge, thereby decreasing DNA binding. These cartridge designs may also be fabricated in glass using a laminate process similar to one employed here, with the exception of bonding layers using a thermal process. Glass fabricated microchannels would also permit higher pressure to be used, dramatically reducing the processing time.

NAFION-Based DNA Extraction

FIG. 15c shows a NAFION-coated electrode based nucleic acid extraction method. A NAFION film (perfluorinated resin; NAFION® is a registered trademark of E. I. du Pont de Nemours and Company) can be applied to gold electrodes on a substrate to electrostatically bind and release nucleic acid. First, lysate is introduced into the electric field region, which traps the nucleic acid to the NAFION-passivated gold electrodes. Passivation with NAFION maintains nucleic acid integrity and prevents electrode degradation by preventing the nucleic acid from reaching the highly reactive electrode surface. The pores in the NAFION film were sufficiently small to prevent DNA migration while allowing ion mobility of cations to the electrode surface. See Lee et al. Next, the trapped electrodes can be rinsed to remove contaminants and excess lysate. Finally, reversal of the applied field releases the purified nucleic acid from the electrodes.

Figure 16C:
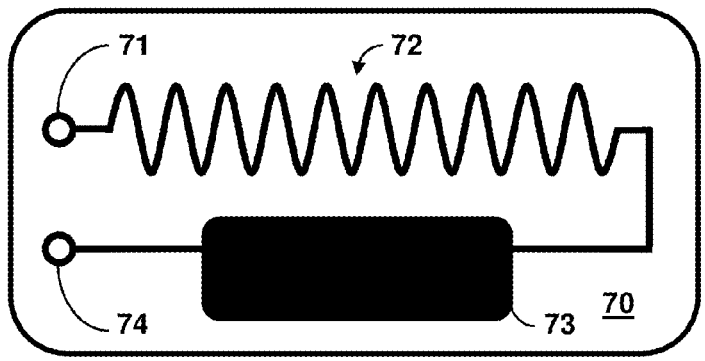

FIG. 16c shows a top-view schematic illustration of an implementation of microfluidic cell lysis and NAFION-coated electrode nucleic acid extraction in a microfluidic cartridge 70. Whole cells in a solution enter the microfluidic channel through an inlet 71. The cells can be acoustically lysed in a lysis portion 72. An array of acoustic transducers (not shown) disposed on the channel couples acoustic energy into the lysis portion 72, causing the whole cells to lyse therein by localized acoustic pressure. As shown, a serpentine channel can be used to increase the exposure time to the acoustic pressure field in the lysis portion 72. Lysate flows out of the lysis portion 72 into the nucleic acid extraction portion 73, comprising opposing NAFION-coated electrodes. A positive bias can be applied to one of the electrodes, which traps the nucleic acid in the lysate to the NAFION-passivated gold electrodes. Subsequent steps can include rinsing of the trapped electrodes and elution of the absorbed nucleic acid by reversal of the applied bias. In each step, excess lysate or eluted nucleic acid can exit the channel through an outlet 74.

Figure 19:
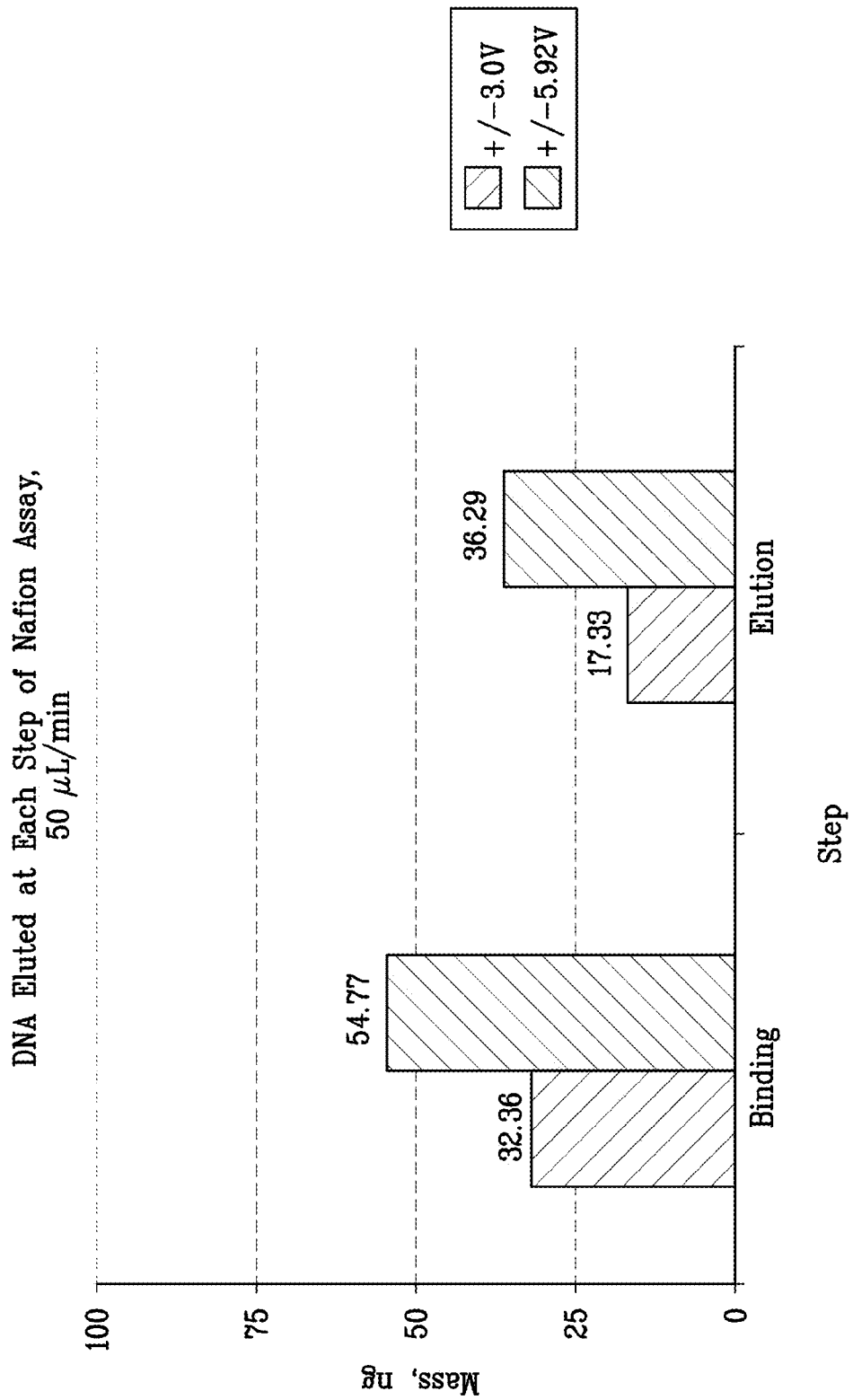
FIG. 19 shows DNA extraction from NAFION-coated electrodes. Increasing the applied voltage dramatically improved DNA binding. The injected amount of DNA was 90 ng.

A microfluidic cartridge incorporating a NAFION-coated gold electrode was fabricated based on the electric field nucleic acid extraction method of Lee et al. The channels were 100 µm in height and 500 µm in width. The electrodes were fabricated by evaporating 200 Å of Cr and 5000 Å of Au onto 100 µm thick Mylar discs. The estimated thickness of the NAFION film was 12 µm. The cartridges were manufactured in a fashion similar to the devices described previously, with the addition of a NAFION-coated gold electrode with an available surface area of 141 mm$^2$ for DNA binding. For each experiment, 50 µL of *E. coli* genomic DNA in 10 mM TE buffer (10 mM Tris-CI pH 7.4, 1 mM EDTA pH 8.0) was injected into the microfluidic channel at a 50 µL/min flow rate. Once the solution entered the channel, a positive voltage was applied to the NAFION-coated electrode to bind DNA. The voltage was applied until all of the solution has run through the channel, at which time the power supply was turned off. 50 µL of 10 mM TE buffer was then loaded into the channel at a 50 µL/min flow rate, and a positive voltage was once again applied to the electrode to keep the DNA bound until the entire volume of buffer had exited the channel. For the elution step, 50 µL of 10 mM TE buffer was loaded into the channel at a 50 µL/min flow rate and a negative voltage was applied to release bound DNA from the electrode. The eluent from each step was collected and analyzed for DNA content using an assay. The voltages for binding and elution of DNA were chosen based on electric field calculations and ranged from +/−2.5 V to +/−7.92 V. As shown in FIG. 19, the amount of DNA was determined during the bound, wash and elution steps for two applied voltages. The total injected DNA was 90 ng, in which 54.77 ng bound at a voltage of 5.92 V. The extraction efficiency increased to 66.3% when based on the DNA that actually bound and eluted from the NAFION-coated electrodes.

The present invention has been described as a method and device for cell lysis by localized acoustic pressure. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A microfluidic device for acoustic cell lysis, comprising:
   a channel formed in a microfluidic substrate, adapted to flow a fluid comprising biological cells therein; and
   at least one acoustic transducer disposed on a lysis portion of the channel, adapted to propagate an acoustic wave in the fluid and thereby generate sufficient localized acoustic pressure in the lysis portion to lyse the biological cells in the fluid by acoustic pressure, wherein the operating frequency of the at least one acoustic transducer is between 10 and 100 MHz.

2. The device of claim 1, wherein the wavelength of the acoustic wave is comparable to the size of the biological cells.

3. The device of claim 1, wherein the height of the channel is less than ten wavelengths of the acoustic wave.

4. The device of claim 1, wherein the height of the channel is less than 100 microns.

5. The device of claim 1, wherein the at least one acoustic transducer is disposed on a separate array substrate that is reversibly coupled to a microfluidic cartridge comprising the channel formed in the microfluidic substrate.

6. The device of claim 1, further comprising a heat sink disposed thermally proximate the at least one acoustic transducer and the channel for removal of heat from the device.

7. The device of claim 1, wherein the microfluidic substrate comprises a glass, ceramic, or a silicon-based material.

8. The device of claim 1, wherein the microfluidic substrate comprises a plastic.

9. The device of claim 1, wherein the channel comprises a straight channel.

10. The device of claim 1, wherein the channel comprises a circuitous pattern.

11. The device of claim 1, further comprising a nucleic acid extraction portion formed in the substrate downstream from the lysis portion, adapted to extract nucleic acid from the lysate.

12. The device of claim 11, wherein the nucleic acid extraction portion comprises means for extracting the nucleic acid from the lysate using a sol-gel/silica bead matrix.

13. The device of claim 11, wherein the nucleic acid extraction portion comprises means for extracting the nucleic acid from the lysate using nucleic acid binding magnetic beads.

14. The device of claim 11, wherein the nucleic acid extraction portion comprises means for extracting the nucleic acid from the lysate using electric field extraction on electrodes coated with a film having pores that are sufficiently small to prevent nucleic acid migration while allowing ion mobility of cations to the electrode surface.

15. The device of claim 14, wherein the film comprises a perfluorinated resin.

16. The device of claim 1, wherein the sufficient localized acoustic pressure is greater than 0.2 MPa.

17. The device of claim 1, wherein the sufficient localized acoustic pressure is greater than 1 MPa.

18. The device of claim 1, wherein the at least one acoustic transducer comprises a 36° Y lithium niobate piezoelectric transducer.

19. The device of claim 1, wherein the power delivered to the lysis portion of the channel by the at least one acoustic transducer is greater than 21.9 dBm.

* * * * *